United States Patent
Hunt

(10) Patent No.: US 12,279,964 B2
(45) Date of Patent: Apr. 22, 2025

(54) IMPLANTS HAVING BONE GROWTH PROMOTING AGENTS AND METHODS OF USING SUCH IMPLANTS TO REPAIR BONE STRUCTURES

(71) Applicant: 4WEB, Inc., Frisco, TX (US)

(72) Inventor: Jessee Hunt, Plano, TX (US)

(73) Assignee: 4WEB, LLC, Dallas, TX (US)

( * ) Notice: Subject to any disclaimer, the term of this patent is extended or adjusted under 35 U.S.C. 154(b) by 790 days.

(21) Appl. No.: 17/370,781

(22) Filed: Jul. 8, 2021

(65) Prior Publication Data

US 2021/0330473 A1 Oct. 28, 2021

Related U.S. Application Data

(63) Continuation-in-part of application No. 16/657,268, filed on Oct. 18, 2019, now Pat. No. 11,510,787, (Continued)

(51) Int. Cl.
*A61F 2/44* (2006.01)
*A61B 17/16* (2006.01)
(Continued)

(52) U.S. Cl.
CPC ........ *A61F 2/4455* (2013.01); *A61B 17/1604* (2013.01); *A61B 17/56* (2013.01);
(Continued)

(58) Field of Classification Search
CPC ........ A61F 2/4455; A61F 2/28; A61F 2/2803; A61F 2/2846; A61F 2/30767;
(Continued)

(56) References Cited

U.S. PATENT DOCUMENTS 3,840,904 A 10/1974 Tronzo
3,867,728 A 2/1975 Stubstad et al.
(Continued)

FOREIGN PATENT DOCUMENTS

CN 201164511 12/2008
CN 201200499 3/2009
(Continued)

OTHER PUBLICATIONS

International Search Report and Written Opinion for PCT/US2020/60759 issued Feb. 17, 2021.
(Continued)

*Primary Examiner* — Ellen C Hammond
*Assistant Examiner* — Tara Rose E Carter
(74) *Attorney, Agent, or Firm* — Kowert, Hood, Munyon, Rankin & Goetzel PC; Gareth M. Sampson

(57) ABSTRACT

Various embodiments of implant systems and related apparatus, and methods of operating the same are described herein. In various embodiments, an implant for interfacing with a bone structure includes a web structure, including a space truss, configured to interface with human bone tissue. The space truss includes two or more planar truss units having a plurality of struts joined at nodes. Implants may be coated with or include fibers or particles to enhance bone growth around and through the implant.

16 Claims, 14 Drawing Sheets

Related U.S. Application Data which is a continuation of application No. 15/721,940, filed on Oct. 1, 2017, now abandoned, which is a continuation of application No. 14/743,555, filed on Jun. 18, 2015, now Pat. No. 9,999,516, which is a continuation of application No. 12/960,092, filed on Dec. 3, 2010, now Pat. No. 9,421,108, which is a continuation of application No. 12/640,825, filed on Dec. 17, 2009, now Pat. No. 8,430,930.

(60) Provisional application No. 63/049,122, filed on Jul. 8, 2020, provisional application No. 61/138,707, filed on Dec. 18, 2008.

(51) Int. Cl.

| | | |
|---|---|---|
| *A61B 17/56* | (2006.01) | |
| *A61B 17/58* | (2006.01) | |
| *A61B 17/68* | (2006.01) | |
| *A61F 2/28* | (2006.01) | |
| *A61F 2/30* | (2006.01) | |
| *A61F 2/32* | (2006.01) | |
| *A61F 2/38* | (2006.01) | |
| *A61F 2/40* | (2006.01) | |
| *A61F 2/42* | (2006.01) | |
| *A61F 2/46* | (2006.01) | |
| *A61B 17/02* | (2006.01) | |
| *A61F 2/36* | (2006.01) | |
| *B33Y 70/00* | (2020.01) | |
| *B33Y 80/00* | (2015.01) | |

(52) U.S. Cl.
CPC .............. *A61B 17/58* (2013.01); *A61B 17/68* (2013.01); *A61F 2/28* (2013.01); *A61F 2/2803* (2013.01); *A61F 2/2846* (2013.01); *A61F 2/30767* (2013.01); *A61F 2/30771* (2013.01); *A61F 2/30907* (2013.01); *A61F 2/32* (2013.01); *A61F 2/38* (2013.01); *A61F 2/40* (2013.01); *A61F 2/4202* (2013.01); *A61F 2/4225* (2013.01); *A61F 2/447* (2013.01); *A61B 2/4611* (2013.01); *A61B 17/025* (2013.01); *A61F 2002/2817* (2013.01); *A61F 2002/2835* (2013.01); *A61F 2002/30153* (2013.01); *A61F 2002/30156* (2013.01); *A61F 2002/30158* (2013.01); *A61F 2002/30179* (2013.01); *A61F 2002/30273* (2013.01); *A61F 2002/30275* (2013.01); *A61F 2002/3028* (2013.01); *A61F 2002/30281* (2013.01); *A61F 2002/30593* (2013.01); *A61F 2002/30599* (2013.01); *A61F 2002/30841* (2013.01); *A61F 2002/30899* (2013.01); *A61F 2002/30909* (2013.01); *A61F 2002/30914* (2013.01); *A61F 2002/3092* (2013.01); *A61F 2/3094* (2013.01); *A61F 2002/30943* (2013.01); *A61F 2002/30952* (2013.01); *A61F 2002/30953* (2013.01); *A61F 2002/30957* (2013.01); *A61F 2002/30962* (2013.01); *A61F 2002/30968* (2013.01); *A61F 2002/3097* (2013.01); *A61F 2/36* (2013.01); *A61F 2002/4628* (2013.01); *A61F 2210/0076* (2013.01); *A61F 2230/0063* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01); *A61F 2310/00179* (2013.01); *A61F 2310/00598* (2013.01); *A61F 2310/00796* (2013.01); *A61F 2310/00958* (2013.01); *A61F 2310/0097* (2013.01); *A61F 2310/00976* (2013.01); *B33Y 70/00* (2014.12); *B33Y 80/00* (2014.12)

(58) Field of Classification Search
CPC .... A61F 2/30771; A61F 2/30907; A61F 2/32; A61F 2/40; A61F 2/4202; A61F 2/4225; A61B 17/1604
USPC ............................................ 623/17.11–17.16
See application file for complete search history.

(56) References Cited

U.S. PATENT DOCUMENTS

| | | |
|---|---|---|
| 4,129,903 A | 12/1978 | Huggler |
| 4,686,970 A | 8/1987 | Dove et al. |
| 4,820,305 A | 4/1989 | Harms et al. |
| 4,863,474 A | 9/1989 | Brown et al. |
| 4,904,261 A | 2/1990 | Dove et al. |
| 4,938,771 A | 7/1990 | Vecsei et al. |
| 5,030,233 A | 7/1991 | Ducheyne |
| 5,108,435 A | 4/1992 | Gustavson et al. |
| 5,147,402 A | 9/1992 | Bohler et al. |
| 5,201,768 A | 4/1993 | Caspari et al. |
| 5,282,861 A | 2/1994 | Kaplan |
| 5,306,149 A | 4/1994 | Schmid et al. |
| 5,336,266 A | 8/1994 | Caspari et al. |
| 5,433,750 A | 7/1995 | Gradinger et al. |
| 5,571,185 A | 11/1996 | Schug |
| 5,609,635 A | 3/1997 | Michelson |
| 5,609,637 A | 3/1997 | Biedermann et al. |
| 5,676,700 A | 10/1997 | Black et al. |
| 5,702,449 A | 12/1997 | McKay |
| 5,702,451 A | 12/1997 | Biedermann et al. |
| 5,879,385 A | 3/1999 | Crockard et al. |
| 5,897,556 A | 4/1999 | Drewry et al. |
| 5,954,504 A | 9/1999 | Misch et al. |
| 5,989,290 A | 11/1999 | Biedermann et al. |
| 6,010,502 A | 1/2000 | Bagby |
| 6,090,732 A | 7/2000 | Ita et al. |
| 6,143,032 A | 11/2000 | Schafer et al. |
| 6,149,689 A | 11/2000 | Grundei et al. |
| 6,206,924 B1 | 3/2001 | Timm |
| 6,245,108 B1 | 6/2001 | Biscup |
| 6,245,110 B1 | 6/2001 | Grundei et al. |
| 6,264,695 B1 | 7/2001 | Stoy |
| 6,280,478 B1 | 8/2001 | Richter et al. |
| 6,290,726 B1 | 9/2001 | Pope et al. |
| 6,379,385 B1 | 4/2002 | Kalas et al. |
| 6,464,727 B1 | 10/2002 | Sharkey et al. |
| 6,520,997 B1 | 2/2003 | Pekkarinen et al. |
| 6,585,770 B1 | 7/2003 | White et al. |
| 6,660,041 B1 | 12/2003 | Grundei |
| 6,712,852 B1 | 3/2004 | Chung et al. |
| 6,730,252 B1 | 5/2004 | Teoh et al. |
| D493,533 S | 7/2004 | Blain |
| 6,761,738 B1 | 7/2004 | Boyd |
| 6,866,682 B1 | 3/2005 | An et al. |
| 6,881,228 B2 | 4/2005 | Zdeblick et al. |
| 6,931,812 B1 | 8/2005 | Lipscomb |
| 6,972,019 B2 | 12/2005 | Michelson |
| 7,156,874 B2 | 1/2007 | Paponneau et al. |
| 7,163,560 B2 | 1/2007 | Mason |
| 7,163,561 B2 | 1/2007 | Michelson |
| 7,208,222 B2 | 4/2007 | Rolfe et al. |
| 7,291,149 B1 | 11/2007 | Michelson |
| 7,537,616 B1 | 5/2009 | Branch et al. |
| 7,572,293 B2 | 8/2009 | Rhodes et al. |
| 7,578,850 B2 | 8/2009 | Kuczynski et al. |
| 7,621,950 B1 | 11/2009 | Globerman et al. |
| 7,846,296 B2 | 12/2010 | Oglaza et al. |
| 8,062,365 B2 | 11/2011 | Schwab |
| 8,292,967 B2 | 10/2012 | Brown et al. |
| 8,430,930 B2 | 4/2013 | Hunt |
| 8,906,074 B2 | 12/2014 | Kang |
| 8,998,990 B2 | 4/2015 | Bertagnoli et al. |
| 9,271,845 B2 | 3/2016 | Hunt |

(56) References Cited

U.S. PATENT DOCUMENTS

| | | |
|---|---|---|
| 9,421,108 B2 | 8/2016 | Hunt |
| 9,545,317 B2 | 1/2017 | Hunt |
| 9,549,823 B2 | 1/2017 | Hunt |
| 9,572,669 B2 | 2/2017 | Hunt |
| 9,636,226 B2 | 5/2017 | Hunt |
| 9,757,235 B2 | 9/2017 | Hunt |
| 9,968,463 B2 | 5/2018 | Liu |
| 9,987,137 B2 | 6/2018 | Hunt |
| 9,999,516 B2 | 6/2018 | Hunt |
| 2002/0169066 A1 | 11/2002 | Cassidy et al. |
| 2002/0183858 A1 | 12/2002 | Contiliano et al. |
| 2003/0078660 A1 | 4/2003 | Clifford et al. |
| 2004/0082999 A1 | 4/2004 | Mathys et al. |
| 2004/0121451 A1 | 6/2004 | Mortiz et al. |
| 2004/0236336 A1 | 11/2004 | Foerster |
| 2004/0252382 A1 | 12/2004 | Nagata |
| 2005/0004572 A1 | 1/2005 | Bidermann et al. |
| 2005/0015154 A1* | 1/2005 | Lindsey .............. A61B 17/68 606/76 |
| 2005/0033425 A1 | 2/2005 | Schwab |
| 2005/0090900 A1 | 4/2005 | Nordquist |
| 2005/0129726 A1 | 6/2005 | Liebschner |
| 2005/0143827 A1 | 6/2005 | Globerman et al. |
| 2005/0171613 A1 | 8/2005 | Sartorius et al. |
| 2005/0222683 A1 | 10/2005 | Berry |
| 2006/0074488 A1 | 4/2006 | Abdou |
| 2006/0106461 A1 | 5/2006 | Embry et al. |
| 2006/0141012 A1 | 6/2006 | Gingras |
| 2006/0147332 A1 | 7/2006 | Jones et al. |
| 2006/0173542 A1 | 8/2006 | Shikinami |
| 2006/0182780 A1 | 8/2006 | Riley et al. |
| 2006/0200062 A1 | 9/2006 | Saadat |
| 2006/0241776 A1* | 10/2006 | Brown ............... A61B 17/7225 623/22.32 |
| 2006/0282166 A1* | 12/2006 | Molz .................... A61F 2/442 623/17.13 |
| 2007/0027544 A1 | 2/2007 | McCord et al. |
| 2007/0032876 A1 | 2/2007 | Clark |
| 2007/0040478 A1 | 2/2007 | Tofail et al. |
| 2007/0055376 A1 | 3/2007 | Michelson |
| 2007/0083268 A1 | 4/2007 | Teoh et al. |
| 2007/0106383 A1 | 5/2007 | Abdou |
| 2007/0129806 A1 | 6/2007 | Harms et al. |
| 2007/0179610 A1 | 8/2007 | Biedermann et al. |
| 2007/0191834 A1 | 8/2007 | Bruneau et al. |
| 2007/0233248 A1 | 10/2007 | Schwab et al. |
| 2007/0255420 A1 | 11/2007 | Johnson et al. |
| 2007/0255422 A1 | 11/2007 | Wei et al. |
| 2007/0270956 A1 | 11/2007 | Heinz |
| 2008/0014457 A1 | 1/2008 | Gennaro et al. |
| 2008/0021461 A1 | 1/2008 | Barker et al. |
| 2008/0039948 A1 | 2/2008 | Biedermann et al. |
| 2008/0071356 A1 | 3/2008 | Greenhalgh et al. |
| 2008/0075752 A1 | 3/2008 | Ratner et al. |
| 2008/0154314 A1 | 6/2008 | McDevitt |
| 2008/0221594 A1 | 9/2008 | Hamman et al. |
| 2009/0041838 A1 | 2/2009 | Guimberteau et al. |
| 2009/0054987 A1 | 2/2009 | Chin |
| 2009/0076508 A1 | 3/2009 | Weinans et al. |
| 2009/0138015 A1 | 5/2009 | Conner et al. |
| 2009/0149947 A1 | 6/2009 | Frohwitter |
| 2009/0149956 A1 | 6/2009 | Greenhalgh et al. |
| 2009/0182336 A1 | 7/2009 | Brenzel et al. |
| 2009/0222098 A1 | 9/2009 | Trieu et al. |
| 2009/0228112 A1 | 9/2009 | Clark et al. |
| 2009/0276048 A1 | 11/2009 | Chirico et al. |
| 2009/0317447 A1 | 12/2009 | Hsiao et al. |
| 2009/0326657 A1 | 12/2009 | Grinberg |
| 2010/0094292 A1 | 4/2010 | Parrott |
| 2010/0106194 A1 | 4/2010 | Bonutti |
| 2010/0161061 A1 | 6/2010 | Hunt |
| 2010/0174377 A1 | 7/2010 | Heuer |
| 2010/0174380 A1 | 7/2010 | Lewis |
| 2010/0179667 A1 | 7/2010 | Day et al. |
| 2010/0228355 A1 | 9/2010 | Linares |
| 2010/0298950 A1 | 11/2010 | McDonnel et al. |
| 2011/0022180 A1 | 1/2011 | Melkent et al. |
| 2011/0035020 A1 | 2/2011 | Laughner et al. |
| 2011/0076316 A1 | 3/2011 | Sivananthan et al. |
| 2011/0118852 A1 | 5/2011 | Evans |
| 2011/0125284 A1 | 5/2011 | Gabbrielli et al. |
| 2011/0196495 A1 | 8/2011 | Hunt |
| 2011/0218585 A1 | 9/2011 | Krinke |
| 2011/0251690 A1 | 10/2011 | Berger |
| 2011/0264229 A1 | 10/2011 | Donner |
| 2011/0307073 A1 | 12/2011 | Teoh et al. |
| 2011/0313532 A1 | 12/2011 | Hunt |
| 2012/0290089 A1 | 11/2012 | Melamed |
| 2013/0030529 A1 | 1/2013 | Hunt |
| 2013/0030540 A1 | 1/2013 | Leibinger |
| 2013/0123935 A1 | 5/2013 | Hunt |
| 2013/0158672 A1 | 6/2013 | Hunt |
| 2013/0184835 A1 | 7/2013 | Ferrari et al. |
| 2013/0218282 A1 | 8/2013 | Hunt |
| 2014/0121776 A1 | 5/2014 | Hunt |
| 2014/0277569 A1 | 9/2014 | Lange |
| 2014/0288649 A1 | 9/2014 | Hunt |
| 2014/0288650 A1 | 9/2014 | Hunt |
| 2015/0282933 A1 | 10/2015 | Hunt |
| 2015/0282945 A1 | 10/2015 | Hunt |
| 2015/0282946 A1 | 10/2015 | Hunt |
| 2016/0081803 A1 | 3/2016 | McKay |
| 2016/0081807 A1 | 3/2016 | Estes et al. |
| 2016/0287389 A1 | 10/2016 | Hunt |
| 2016/0287404 A1 | 10/2016 | Hunt |
| 2016/0287405 A1 | 10/2016 | Hunt |
| 2016/0338842 A1 | 11/2016 | Adams |
| 2017/0042697 A1 | 2/2017 | McShane, III et al. |
| 2017/0157299 A1 | 6/2017 | Janko et al. |
| 2017/0216035 A1 | 8/2017 | Hunt |
| 2017/0319344 A1 | 11/2017 | Hunt |
| 2017/0360563 A1 | 12/2017 | Hunt |
| 2018/0064540 A1 | 3/2018 | Hunt |
| 2018/0085230 A1 | 3/2018 | Hunt |
| 2019/0060077 A1 | 2/2019 | Hunt |
| 2019/0099515 A1 | 4/2019 | Bagga et al. |
| 2019/0151114 A1 | 5/2019 | Sack |
| 2020/0155326 A1 | 5/2020 | Hunt |

FOREIGN PATENT DOCUMENTS

| | | | |
|---|---|---|---|
| DE | 19543530 | 5/1997 | |
| DE | 19721661 | 11/1998 | |
| DE | 10120330 A1 | 11/2002 | |
| DE | 202006015414 U1 | 11/2006 | |
| DE | 202006015415 U1 | 11/2006 | |
| DE | 102006047663 | 4/2008 | |
| EP | 0396883 A2 | 11/1990 | |
| EP | 0268115 | 1/1991 | |
| EP | 0489684 | 6/1992 | |
| EP | 0561263 | 9/1993 | |
| EP | 1925271 A1 | 5/2008 | |
| JP | 52-148995 | 12/1977 | |
| JP | Hei06-503990 | 5/1994 | |
| JP | 2002-536046 | 10/2002 | |
| JP | 2003-511198 | 3/2003 | |
| JP | 2007-167665 | 7/2007 | |
| JP | 2008-539817 | 11/2008 | |
| JP | 2009-006186 | 1/2009 | |
| JP | 2009112719 | 5/2009 | |
| JP | 2012520120 | 9/2012 | |
| WO | 2001028460 | 4/2001 | |
| WO | 02071986 A2 | 9/2002 | |
| WO | WO-03057086 A2 * | 7/2003 | ............ A61L 24/02 |
| WO | 2005009729 | 2/2005 | |
| WO | 2007048817 A1 | 5/2007 | |
| WO | 2008022206 | 2/2008 | |
| WO | 2008146141 A2 | 12/2008 | |
| WO | 2009144434 | 12/2009 | |
| WO | 2010080511 | 7/2010 | |
| WO | 2012010327 | 1/2012 | |
| WO | 2013006778 | 1/2013 | |

(56) References Cited

FOREIGN PATENT DOCUMENTS

OTHER PUBLICATIONS

International Search Report and Written Opinion for PCT/US2021/023782 issued Jul. 1, 2021.
Office Action for U.S. Appl. No. 13/762,825 issued Mar. 7, 2016.
Office Action for U.S. Appl. No. 13/762,825 issued Sep. 20, 2016.
International Search Report and Written Opinion for PCT/US2013/025281 issued May 15, 2013.
International Preliminary Report on Patentability for PCT/US2013/025281 issued Aug. 12, 2014.
Australian Examination Report for AU Application No. 2013216947 dated Mar. 27, 2017.
Australian Examination Report for AU Application No. 2013216947 dated Feb. 16, 2018.
Canadian Examination Report for CA Application No. 2,863,865 dated Oct. 5, 2018.
Canadian Examination Report for CA Application No. 2,863,865 dated Jun. 5, 2020.
European Examination Report for EP Application No. 13746753.6 dated Sep. 23, 2015.
European Examination Report for EP Application No. 13746753.6 dated Oct. 28, 2016.
Japanese Examination Report for JP Application No. 2014-556705 dated Nov. 29, 2016.
Japanese Examination Report for JP Application No. 2014-556705 dated Sep. 19, 2017.
Office Action for U.S. Patent No. U.S. Appl. No. 15/463,458 issued Dec. 26, 2017.
Final Office Action for U.S. Patent No. U.S. Appl. No. 15/463,458 issued Oct. 24, 2018.
Japanese Examination Report for JP Application No. 2018-006991 dated Nov. 20, 2018.
Japanese Examination Report for JP Application No. 2018-006991 dated Nov. 12, 2019.
Australian Examination Report for AU Application No. 2018202175 dated Nov. 22, 2018.
Australian Examination Report for AU Application No. 2018202175 dated Aug. 23, 2019.
Office Action for U.S. Appl. No. 14/036,974 issued Jul. 22, 2015.
International Search Report and Written Opinion for PCT/US2013/061725 issued Jan. 13, 2014.
International Preliminary Report on Patentability for PCT/US2013/061725 issued Mar. 13, 2015.
Canadian Examination Report for CA Application No. 2,889,063 dated Sep. 20, 2019.
Canadian Examination Report for CA Application No. 2,889,063 dated Jul. 31, 2020.
Chinese Examination Report for CN Application No. 201300555597.3 dated Apr. 5, 2016.
Chinese Examination Report for CN Application No. 201300555597.3 dated Nov. 16, 2016.
Chinese Examination Report for CN Application No. 201300555597.3 dated Jun. 8, 2017.
Extended European Search Report for European Application No. 13843010.3 dated Apr. 16, 2019.
Third Party Observations for European Application No. 13843010.3 dated Jan. 30, 2020.
Korean Office Action for Korean Application No. 10-2015-7010324 dated May 18, 2020.
Japanese Examination Report for JP Application No. 2013-533302 dated Aug. 15, 2017.
Australian Examination Report for AU Application No. 2013323602 dated Jul. 4, 2017.
Office Action for U.S. Appl. No. 14/215,961 issued Mar. 11, 2016.
International Search Report and Written Opinion for PCT/US2014/030319 issued Apr. 6, 2015.
International Preliminary Report on Patentability for PCT/US2014/030319 issued Sep. 15, 2015.
Office Action for U.S. Appl. No. 14/216,087 issued Aug. 27, 2015.
Office Action for U.S. Appl. No. 14/216,087 issued Jul. 14, 2016.
Office Action for U.S. Appl. No. 14/216,087 issued Feb. 2, 2017.
International Search Report and Written Opinion for PCTUS201430358 issued Aug. 27, 2014.
International Preliminary Report on Patentability for PCTUS201430358 issued Sep. 15, 2015.
Canadian Examination Report for CA Application No. 2,911,880 dated Mar. 26, 2021.
Chinese Examination Report for CN Application No. 201480026652.0 dated Dec. 2, 2016.
Chinese Examination Report for CN Application No. 201480026652.0 dated Jul. 31, 2017.
European Examination Report for EP Application No. 14762747 dated Jan. 26, 2017.
Japanese Examination Report for JP Application No. 2016-503373 dated Jan. 29, 2018.
Japanese Examination Report for JP Application No. 2016-503373 dated Dec. 17, 2018.
Korean Office Action for KR Application No. 10-2015-7029384 dated Oct. 22, 2020.
Japanese Examination Report for JP Application No. 2019-147711 dated Jul. 22, 2020.
Office Action issued in Canadian Application No. 2,911,880 dated Mar. 26, 2021.
International Search Report and Written Opinion for PCT/US2020/58330 issued Jan. 29, 2021.
"Rapid prototyping enables company to manufacture revolutionary new medical product", accessed at <http://www.newslettersonline.com/user/user.fas/s=63/fp=3/tp=47?T=open_article,565208&P=article>, Oct. 9, 2003. (pp. 1-2).
"Midlantic Medical Systems—Geo Structure Rectangles (Posterior Approach)" accessed Jun. 11, 2008 at <http://www.midlanticmedical.com/products/anteriorColumnSpacers.php?p=2>. (p. 1).
"Midlantic Medical Systems—Nexus (Transverse Approach)" accessed Jun. 11, 2008 at <http://www.midlanticmedical.com/products/anteriorColumnSpacers.php?p=4>. (p. 1).
"Zimmer® Trabecular Metal™ Technology", accessed at <http://www.zimmerindia.com/z/ctl/op/global/action/1/id/9512/template/PC/navid/8173>, Jul. 9, 2006. (pp. 1-5).
"Multifunctional Electrochemical Energy Storage Materials", accessed on Oct. 1, 2008 at <http://www.uvapf.org/technologies/index.cfm/fuseaction/invention/invention_id/85/?CFID=1785971&CFTOKEN=59649784&>. (pp. 1-2).
"Image: C60a.phg", Wikipedia, accessed on Oct. 1, 2008 at <http://en.wikipedia.org/wiki/Image:C60a.png"> (pp. 1-3).
"Image:POV-Ray-Dodecahedron.svg", Wikipedia, accessed at on Oct. 1, 2008 at <http://en.wikipedia.org/wiki/Image:POV-Ray-Dodecahedron.svg>. (pp. 1-4).
"Image:Icosahedron.svg", Wikipedia, accessed on Oct. 1, 2008 at <http://en.wikipedia.org/wiki/Image:Icosahedron.svg>. (pp. 1-2).
"Image:Octahedron.svg", Wikipedia, accessed on Oct. 1, 2008 at <http://en.wikipedia.org/wiki/Image:Octahedron.svg>. (pp. 1-3).
"Truss" Wikipedia, accessed at <http://en.wikipedia.org/wiki/Truss>, Dec. 16, 2009. (pp. 1-9).
"NexGen Trabecular Metal Tibial Cone Augments" accessed at <http://catalog.zimmer.com/content/zpc/products/200/250/C60/CE008/2653.html>, Nov. 17, 2009. (p. 1).
"Spinal Kinetics", accessed on Oct. 6, 2009 at <http://www.spinalkinetics.com/m6systems.html>. (p. 1).
"Cinn", accessed on Oct. 6, 2009 at <http://www.cinn.org/cr-articles/CR-artificial-disc.html>, Copyright 2008. (pp. 1-9).
"Zimmer Anatomical Shoulder Fracture System", copyright 2007. (pp. 1-6).
"Wolff's Law", Wikipedia, accessed at <http://en.wikipedia.org/wiki/Wolff's_law>, Jun. 9, 2010. (pp. 1-2).
"E-Manufacturing is making its inroad to series production", Nov. 20, 2008. (pp. 1-2).
"InFix Anterior Lumbar Device" Dec. 17, 2009. (p. 1).
"Biofoam Wedge System" Wright, Copyright 2010. (pp. 1-4).
"LPT2 Great Toe Implant" Wright, Copyright 2008. (p. 1-16).
"Biofoam Wedge System Surgical Technique" Wright, Copyright 2010. (pp. 1-12).

(56) References Cited

OTHER PUBLICATIONS

Murr et al. "Next-generation biomedical implants using additive manufacturing of complex, cellular and functional mesh arrays", Philosophical Transactions of the Royal Society, Mar. 22, 2010, vol. 368, No. 1917, pp. 1999-2032.
Yan, et al. "Mechanical strain regulates osteoblast proliferation through integrin-mediated ERK activation", PloS One, Apr. 23, 2012, vol. 7, No. 4, Article No. e35709.
Distension Blog located at htpp://kineticdistensio.blogspot.com/2011_10_0_archive.html including entry of Oct. 14, 2011.
Baranovskaya et al. Itech M. Sc. Programme-Uni Stuttgart, Institut Fur Computerbasiertes Entwerfen (ICD, Stuttgart, Germany located at htpp:/architecture-is-yes.tumblr.com/post/8525760 accessed Aug. 21, 2015.
Cobos et al. "The Cylindrical Titanium Mesh Cage for Treatment of a Long Bone Segmental Defect: Description of a New Technique and Report of Two Cases" Journal of Orthopaedic Trauma (2000) vol. 14, No. 1, pp. 54-59.
Lindsey et al. "The Efficacy of Cylindrical Titanium Mesh Cage for the Reconstruction of a Critical-Size Canine Segmental Remoral Diaphyseal Defect" Journal of Orthopaedic Research (Jul. 2006), pp. 1438-1453.
Office Action for U.S. Appl. No. 12/640,825 issued Aug. 30, 2012.
EPO International Search Report and Written Opinion for PCT/US2009/068512 mailed May 12, 2010. (pp. 1-61).
International Preliminary Report on Patentability for PCT/US2009/068512 dated Mar. 31, 2011. (pp. 1-8).
Office Action for U.S. Appl. No. 12/960,092 issued Aug. 20, 2014.
Office Action for U.S. Appl. No. 12/960,092 issued Apr. 24, 2015.
Australian Examination Report for Australian Patent Application No. 2009335771 dated Jan. 14, 2014.
Canadian Examination Report for Canadian Patent Application No. 2,746,505 dated Dec. 1, 2015.
European Examination Report for EP Application No. 09796208.8 dated Feb. 7, 2014.
European Examination Report for EP Application No. 09796208.8 dated Aug. 21, 2014.
Office Action for U.S. Appl. No. 14/743,555 issued Sep. 27, 2016.
Final Office Action for U.S. Appl. No. 14/743,555 issued Jul. 3, 2017.
Office Action for U.S. Appl. No. 14/743,579 issued Apr. 5, 2016.
Office Action for U.S. Appl. No. 14/743,607 issued Apr. 6, 2016.
Final Office Action for U.S. Appl. No. 14/743,607 issued Sep. 12, 2016.
Office Action for U.S. Appl. No. 14/743,607 issued Jun. 7, 2017.
Final Office Action for U.S. Appl. No. 14/743,607 issued Apr. 6, 2018.
Office Action for U.S. Appl. No. 14/743,607 issued Dec. 14, 2018.
Final Office Action for U.S. Appl. No. 14/743,607 issued Jun. 10, 2019.
Office Action for U.S. Appl. No. 14/743,607 issued Jan. 13, 2020.
Final Office Action for U.S. Appl. No. 14/743,607 issued Aug. 4, 2020.
Australian Examination Report for Australian Patent Application No. 2013323602 dated Jul. 4, 2017.
Office Action for U.S. Appl. No. 15/721,940 issued Jun. 29, 2018.
Office Action for U.S. Appl. No. 15/721,940 issued Mar. 26, 2019.
Final Office Action for U.S. Appl. No. 15/721,940 issued Oct. 16, 2019.
Advisory Action for U.S. Appl. No. 15/721,940 issued Mar. 13, 2020.
Office Action for U.S. Appl. No. 15/721,940 issued Jun. 2, 2020.
Office Action for U.S. Appl. No. 12/818,508 issued Feb. 4, 2013.
Final Office Action for U.S. Appl. No. 12/818,508 issued Aug. 15, 2013.
Office Action for U.S. Appl. No. 12/818,508 issued May 22, 2015.
Final Office Action for U.S. Appl. No. 12/818,508 issued Nov. 20, 2015.
Office Action for U.S. Appl. No. 12/818,508 issued Dec. 2, 2016.

EPO International Search Report and Written Opinion for PCT/US2011/040117 mailed Aug. 12, 2011.
International Preliminary Report on Patentability for PCT/US2011/040117 dated Dec. 19, 2012.
Office Action for U.S. Appl. No. 13/805,231 issued Aug. 20, 2015.
Final Office Action for U.S. Appl. No. 13/805,231 issued Dec. 11, 2015.
Office Action for U.S. Appl. No. 13/805,231 issued Oct. 12, 2016.
Final Office Action for U.S. Appl. No. 13/805,231 issued Apr. 25, 2017.
Office Action for U.S. Appl. No. 13/805,231 issued Dec. 18, 2017.
Australian Examination Report for AU Application No. 2011267941 dated Jan. 16, 2014.
Canadian Examination Report for Canadian Patent Application No. 2,803,015 dated Jun. 15, 2017.
Canadian Examination Report for Canadian Patent Application No. 2,803,015 dated Feb. 9, 2018.
Canadian Examination Report for Canadian Patent Application No. 2,803,015 dated Dec. 5, 2019.
Canadian Examination Report for Canadian Patent Application No. 2,803,015 dated Dec. 30, 2020.
European Examination Report for EP Application No. 11726306.1 dated Jan. 7, 2016.
European Examination Report for EP Application No. 11726306.1 dated Nov. 13, 2017.
Japanese Examination Report for JP Application No. 2013-515407 dated Feb. 24, 2015.
Japanese Examination Report for JP Application No. 2013-515407 dated Nov. 24, 2015.
Office Action for U.S. Appl. No. 13/194,561 issued Mar. 19, 2013.
Final Office Action for U.S. Appl. No. 13/194,561 issued Sep. 26, 2013.
Office Action for U.S. Appl. No. 13/194,561 issued Jan. 20, 2015.
International Search Report and Written Opinion for PCT/US2012/048300 May 7, 2013.
International Preliminary Report on Patentability for PCT/US2012/048300 Feb. 4, 2014.
Japanese Examination Report for JP Application No. 2014-523976 dated May 24, 2016.
International Search Report and Written Opinion for PCT/US2012/045717 issued Jan. 30, 2013.
International Preliminary Report on Patentability for PCT/US2012/045717 dated Jan. 7, 2014.
Office Action for U.S. Appl. No. 13/668,968 issued Aug. 18, 2014.
Office Action for U.S. Appl. No. 13/668,968 issued Jan. 7, 2015.
Office Action for U.S. Appl. No. 13/668,968 issued Jun. 29, 2015.
Office Action for U.S. Appl. No. 13/668,968 issued Apr. 14, 2016.
Final Office Action for U.S. Appl. No. 13/668,968 issued Nov. 16, 2016.
International Search Report and Written Opinion for PCT/US2012/063600 issued Jan. 31, 2013.
International Preliminary Report on Patentability for PCT/US2012/063600 issued May 6, 2014.
Australian Examination Report for AU Application No. 2012332092 dated Feb. 14, 2017.
Australian Examination Report for AU Application No. 2012332092 dated Dec. 19, 2017.
Australian Examination Report for AU Application No. 2012332092 dated Feb. 9, 2018.
Canadian Examination Report for Canadian Patent Application No. 2,854,021 dated Jul. 26, 2018.
Supplemental European Search Report for EP Application No. 12846553.1 issued May 20, 2015.
European Office Action for EP Application No. 12846553.1 issued Mar. 17, 2016.
European Office Action for EP Application No. 12846553.1 issued Aug. 19, 2016.
Japanese Examination Report for JP Application No. 2014-540188 dated Jul. 14, 2016.
Australian Examination Report for AU Application No. 2018201065 dated Jul. 20, 2018.
Australian Examination Report for AU Application No. 2018201065 dated Jul. 3, 2019.

(56) References Cited

OTHER PUBLICATIONS

Office Action for U.S. Appl. No. 13/762,825 issued Jul. 2, 2014.
Office Action for U.S. Appl. No. 13/762,825 issued Dec. 12, 2014.
Rosen, Dr. David, et al., Design of General Lattice Structures for Lightweight and Compliance Applications, Jul. 5, 2006, Rapid Manufacturing Conference, Loughborough University, Jul. 5-6, 2006, 14 pgs.
HRL Announces Extraordinary New Lightweight Materials, HRL Laboratories | News, Oct. 29, 2007, 2 pgs.
Lefebvre, Louis-Philippe, et al., Porous Metals and Metallic Foams: Current Status and Recent Developments, Sep. 17, 2008, Advanced Engineering Materials 2008, 10, No. 9, pp. 775-787.
International Search Report and Written Opinion for PCT/US2021/040939 issued Nov. 4, 2021.
Final Office Action in U.S. Appl. No. 17/370,873, dated May 31, 2023, 15 pp.
Office Action in U.S. Appl. No. 17/370,873, dated Nov. 17, 2023, 13 pp.
Final Office Action in U.S. Appl. No. 17/370,873, dated Jun. 5, 2024, 10 pp.
Notice of Allowance in U.S. Appl. No. 17/370,873, dated Sep. 18, 2024, 9 pp.
Office Action in Australian Patent Application No. 2023200653, dated Jun. 24, 2024, 3 pgs.
Extended Search Report in European Application No. 21837378.5, dated Jul. 11, 2024, 7 pgs.
Examination Report No. 1 in Australian Patent Application No. 2024204047, dated Feb. 20, 2025, 3 pp.

\* cited by examiner

IMPLANTS HAVING BONE GROWTH PROMOTING AGENTS AND METHODS OF USING SUCH IMPLANTS TO REPAIR BONE STRUCTURES

PRIORITY CLAIM

This patent application claims priority to U.S. Provisional Patent Application No. 63/049,122 filed Jul. 8, 2020, which is incorporated by reference as if fully set forth herein. This patent application is also a continuation-in-part of U.S. patent application Ser. No. 16/657,268 riled Oct. 18, 2019, which is a continuation of U.S. patent application Ser. No. 15/721,940 filed Oct. 1, 2017, which is a continuation of U.S. patent application Ser. No. 14/743,555 filed Jun. 18, 2015 which is a continuation of U.S. patent application Ser. No. 12/960,092 filed Dec. 3, 2010 which is a continuation of U.S. patent application Ser. No. 12/640,825 filed Dec. 17, 2009, which claims priority to U.S. Provisional Patent Application Ser. No. 61/138,707 filed Dec. 18, 2008, all of which are hereby incorporated by reference in their entirety as though fully and completely set forth herein.

BACKGROUND OF THE INVENTION

1. Field of the Invention

The present invention relates generally to medical devices and, more specifically, to implants.

2. Description of the Relevant Art

Implants may be used in human and/or animals to support and/or secure one or more bones. For example, implants may be used in the spine to support and or replace damaged tissue between the vertebrae in the spine. Once implanted between two vertebrae, the implant may provide support between the two vertebrae and bone growth may take place around and through the implant to at least partially fuse the two vertebrae for long-term support. Implants may include relatively large rims with solid material that may cover, for example, 50% of the area that interacts with the endplate. The rim may provide a contact area between the implant and the vertebral endplates. Large rims may have several drawbacks. For example, large rims may impede bone growth and reduce the size of the bone column fusing the superior and inferior vertebral bodies. Additionally, large rims preferentially support and regionalize loads, preventing distribution of force and accommodating response. The process of localizing loading also serves to under load other areas of the vertebral bodies, thereby activating regional resorption according to negative microstrain.

Spinal implants may include open channels through the center of the supporting rims in a superior/inferior direction. The open channel design may require members of the implant that separate the rims that interact with the vertebral endplates to absorb the compressive forces between the vertebral endplates. This may increase the pressure on smaller areas of the vertebral endplates and may potentially lead to stress risers in the vertebral endplates. Further, while bone graft material is often used in conjunction with implants to encourage bone growth, the open column design of implants may reduce the likelihood of bone graft material from securing itself to the implant which could result in a bio-mechanical cooperation that is not conducive to promoting good fusion.

Bone graft material may be packed into the implant in a high-pressure state to prevent bone graft material from exiting the implant while being placed between the vertebral endplates. The high-pressure state may also reduce the potential for the bone graft material loosening due to motion between the implant and the vertebral endplates or compressive forces experienced during settling of the implant. In addition, a high-pressure environment may allow the bone graft material to re-model and fuse at greater strength. High-pressure states, however, may be difficult to create and maintain for the bone graft material in an implant. In particular, the lack of attachment of the bulk graft cannot fully accept or integrate the differential loading anticipated in normal kinetic scope.

SUMMARY OF THE INVENTION

Various embodiments of implant systems and related apparatus, and methods of operating the same are described herein. In various embodiments, an implant for interfacing with a bone structure includes a web structure, including a space truss, configured to interface with human bone tissue, including cells, matrix, and ionic milieu. The space truss includes two or more planar truss units having a plurality of struts joined at nodes. Bone growth promoting agents may be incorporated into the implant.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
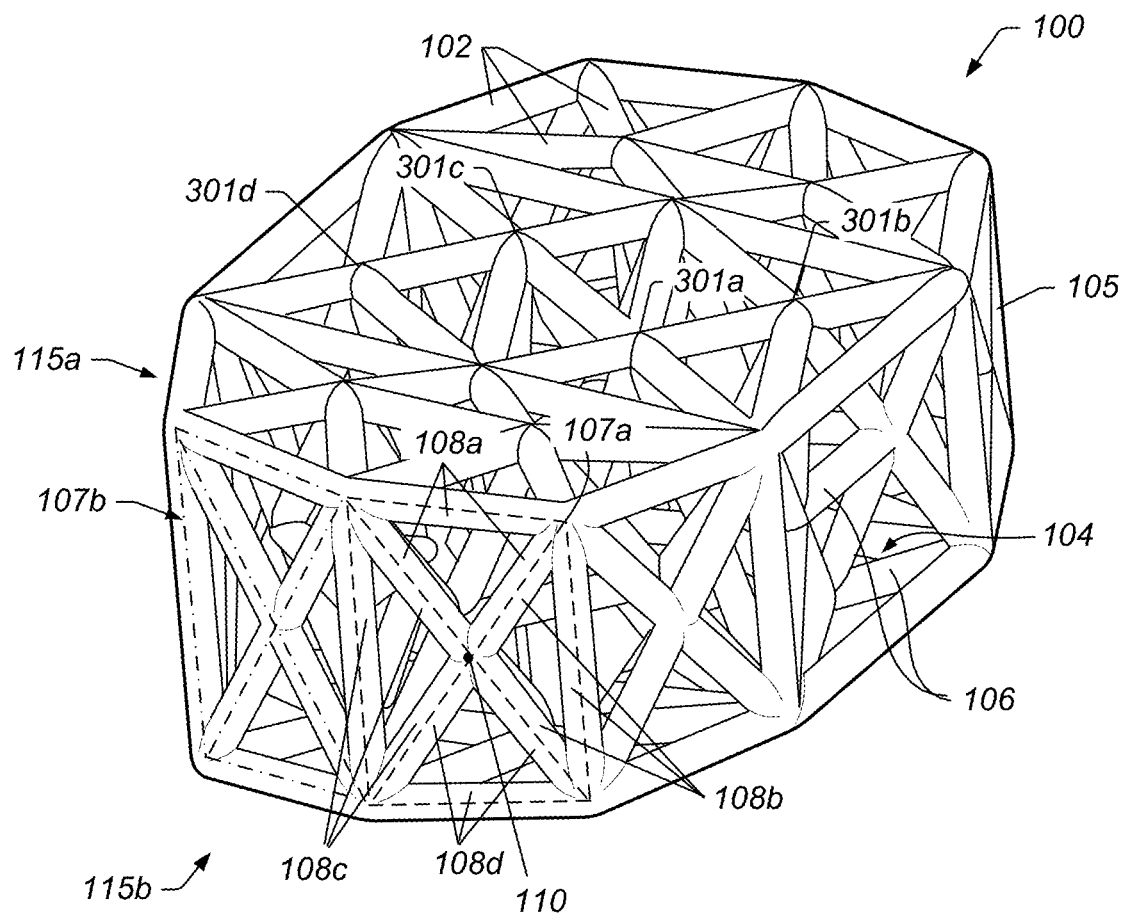
FIGS. 1A-1B illustrate views of an implant with lordosis, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

As used herein a "truss structure" is a structure having one or more elongate struts connected at joints referred to as nodes. Trusses may include variants of a pratt truss, king post truss, queen post truss, town's lattice truss, planar truss, space truss, and/or a vierendeel truss (other trusses may also be used). A "truss unit" is a structure having a perimeter defined by three or more elongate struts."

As used herein a "planar truss" is a truss structure where all of the struts and nodes lie substantially within a single two-dimensional plane. A planar truss, for example, may include one or more "truss units" where each of the struts is a substantially straight member such that the entirety of the struts and the nodes of the one or more truss units He in substantially the same plane. A truss unit where each of the struts is a substantially straight strut and the entirety of the struts and the nodes of the truss unit lie in substantially the same plane is referred to as a "planar truss unit."

As used herein a "space truss" is a truss having struts and nodes that are not substantially confined in a single two-dimensional plane. A space truss may include two or more planar trusses (e.g., planar truss units) wherein at least one of the two or more planar trusses lies in a plane that is not substantially parallel to a plane of at least one or more of the other two or more planar trusses. A space truss, for example, may include two planar truss units adjacent to one another (e.g., sharing a common strut) wherein each of the planar truss units lie in separate planes that are angled with respect to one another (e.g., not parallel to one another).

As used herein a "triangular truss" is a structure having one or more triangular units that are formed by three straight struts connected at joints referred to as nodes. For example, a triangular truss may include three straight elongate strut members that are coupled to one another at three nodes to from a triangular shaped truss. As used herein a "planar triangular truss" is a triangular truss structure where all of the struts and nodes lie substantially within a single two-dimensional plane. Each triangular unit may be referred to as a "triangular truss unit." A triangular truss unit where each of the struts is a substantially straight member such that the entirety of the struts and the nodes of the triangular truss units lie in substantially the same plane is referred to as a "planar triangular truss unit." As used herein a "triangular space truss" is a space truss including one or more triangular truss units.

In accordance with the descriptions herein, in various embodiments, an implant may include a web structure. The web structure for the implant may include a micro truss design. In some embodiments, the micro truss design may include a web structure with multiple struts. Other web structures are also contemplated. The web structure may extend throughout the implant (including a central portion of the implant). The web structure may thus reinforce the implant along multiple planes (including internal implant load bearing) and provide increased area for bone graft fusion. The web structure may be used in implants such as spinal implants, corpectomy devices, hip replacements, knee replacements, long bone reconstruction scaffolding, and cranio-maxillofacial implants foot and ankle, hand and wrist, shoulder and elbow (large joint, small joint, extremities). Other implant uses are also contemplated. In some embodiments, the web structure for the implant may include one or more geometric objects (e.g., polyhedrons), in some embodiments, the web structure may not include a pattern of geometrical building blocks (e.g., an irregular pattern of struts may be used in the implant). In some embodiments, the web structure may include a triangulated web structure including two or more tetrahedrons. A tetrahedron may include four triangular faces in which three of the four triangles meet at each vertex. The web structure may further include two tetrahedrons placed together at two adjacent faces to form a web structure with a hexahedron-shaped frame (including six faces). In some embodiments, multiple hexahedron-shaped web structures may be arranged in a side-by-side manner. The web structures may connect directly through side vertices (e.g., two or more hexahedron-shaped web structures may share a vertex). In some embodiments, the web structure may be angled to provide lordosis to the implant.

Figure 1B:
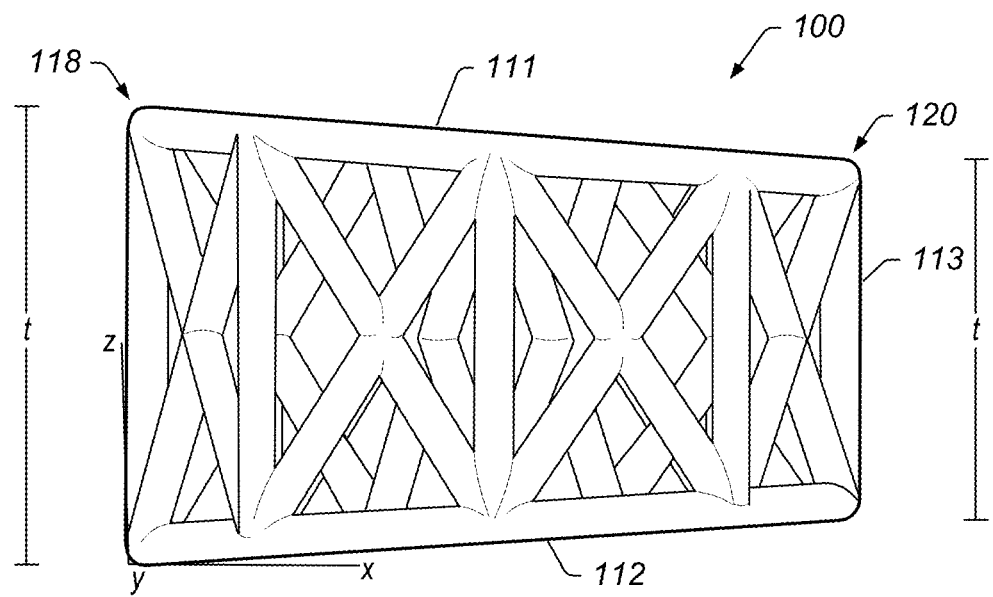

FIGS. 1A-1B illustrate views of implant 100, according to an embodiment. The specifically depicted implant 100 may be used, for example, in anterior lumbar inter-body fusion (AUF) or posterior lumbar inter-body fusion (PLIF), however, it should be understood that implant 100 may have a variety of shapes suitable for bone fusion applications. In some embodiments, implant 100 may include a web structure with one or more trusses 102 (e.g., planar and spree trusses). Implant 100 may be used in various types of implants for humans or animals such as spinal implants, corpectomy devices, knee replacements, hip replacements, long bone reconstruction scaffolding, and cranio-maxifacial implants foot and ankle, hand and wrist, shoulder and elbow (large joint, small joint, extremity as well as custom trauma implants). Other implant uses are also contemplated.

In various embodiments, the trusses 102 of the web structure may include one or more planar truss units (e.g., planar triangular truss units) constructed with straight or curved/arched members (e.g., struts) connected at various nodes. In some embodiments, the trusses 102 may be micro-trusses. A "micro-truss" is a truss having dimensions sufficiently small enough such that a plurality of micro-trusses can be assembled or otherwise coupled to one another to form a web structure having a small enough overall dimension (e.g., height, length and width) such that substantially all of the web structure can be inserted into an implant location (e.g., between two vertebra). Such a web structure and its micro-trusses can thus be employed to receive and distribute throughout the web structure loading forces of the surrounding tissue (e.g., vertebra, bone, or the like). In one embodiment, the diameters of the struts forming the micro-truss may be between about 0.25 millimeters (mm) and 5 mm in diameter (e.g., a diameter of about 0.25 mm, 0.5 mm, 0.6 mm, 0.7 mm, 0.8 mm, 0.9 mm, 1 mm, 2 mm, 3 mm, 4 mm, or 5 mm). In one embodiment, a micro-truss may have an overall length or width of less than about 1 inch (e.g., a length less than about 0.9 in, 0.8 in, 0.7 in, 0.6 in, 0.5 in, 0.4 in, 0.3 in, 0.2 in, 0.1 in).

As depicted, for example, in FIGS. 1A-1B, the web structure may extend throughout implant 100 (including the central portion of implant 100) to provide support throughout implant 100. Trusses 102 of implant 190 may thus support implant 100 against tensile, compressive, and shear forces. Web structure may also reinforce implant 100 along multiple planes. The external truss structure may, for example, provide support against tensile and compressive forces acting vertically through the implant, and the internal web structure may provide support against tensile, compressive, and shear forces along the various planes containing the respective trusses. In some embodiments, the web structure includes trusses 102 that form a triangulated web structure with multiple struts (e.g., struts 103a-f) (struts are generally referred to herein as "struts 103").

In one embodiment, web structure of the implant 100 may include an internal web structure that is at least partially enclosed by an external truss structure. For example, in one embodiment, web structure 101 may include an internal web structure that includes a space truss having at least a portion of the space truss surrounded by an external truss structure that includes one or more planar trusses formed with a plurality of planar truss units that lie substantially in a single plane. FIG. 1A depicts an embodiment of implant 100 having an internal web structure 104 and an external truss structure 105. In the illustrated embodiment, internal web structure 104 includes a space truss defined by a plurality of planar truss units 106 coupled at an angle with respect to one another such that each adjacent truss unit is not co-planar with each adjacent truss units. Adjacent truss units may include two truss units that share a strut and the respective two nodes at the ends of the shared strut.

In one embodiment, external truss structure 105 includes a plurality of planar trusses that are coupled about an exterior, interior or other portion of the implant. For example, in the illustrated embodiment, the external truss structure 105 includes a series of planar trusses 107a,b that arc coupled to one another. Planar truss 107a is denoted by a dashed line [ ~ ~ ~ ~ ~ ], planar truss 107b is denoted by dotted-dashed line [ ~ ˙ ~ ˙ ~ ]. Each planar truss is formed from a plurality of planar truss units (e.g., triangular planar truss units. As depicted, planar truss 107a includes four triangular planar truss units 108a,b,c,d having a common vertex 110 and arranged to form a generally rectangular structure that lies in a single common plane. In other words, the four triangular planar truss units are arranged to form a substantially rectangular structure having "X" shaped struts extend from one corner of the rectangular structure to the opposite corner of the rectangular structure. As depicted, the substantially rectangular structure may include a trapezoidal shape. As described in more detail below, the trapezoidal shape may be conducive to providing an implant including lordosis. Lordosis may include an angled orientation of surfaces (e.g., top and bottom) of an implant that provides for differences in thickness in anterior and posterior regions of the implant such that the implant is conducive for supporting the curvature of a vertebral column.

In one embodiment, the planar trusses that form the external truss are coupled to one another, and are aligned along at least one axis. For example, in FIG. 1A, planar truss section 107a is coupled to an adjacent planar truss 107b. Planer truss sections 107a,b are not parallel in all directions. Planar truss sections 107a,b are, however, arranged parallel to one another in at least one direction (e.g., the vertical direction between the top and the bottom faces of implant 100). For example, planar trusses 107a,b and the additional planar trusses are arranged in series with an angle relative to one another to form a generally circular or polygon shaped enclosure having substantially vertical walls defined by the planar trusses and the planar truss units arranged in the vertical direction.

Figure 2A:
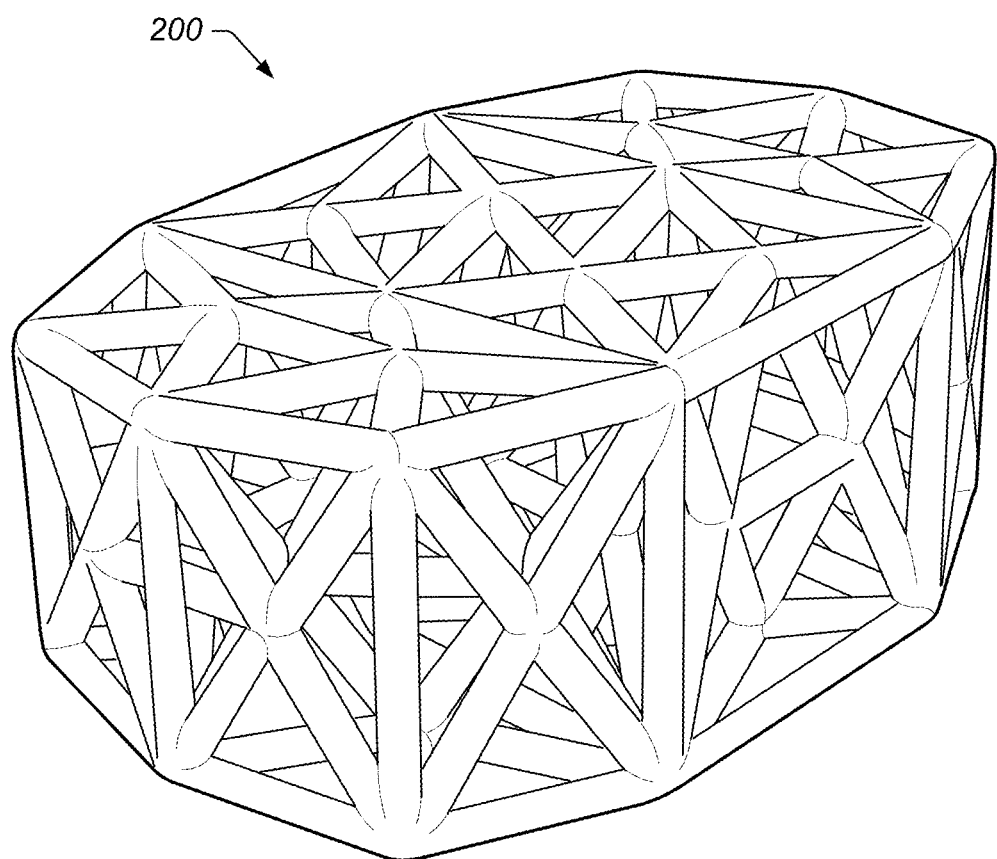
FIGS. 2A-2D illustrate views of an implant without lordosis, according to an embodiment.
Figure 2B:
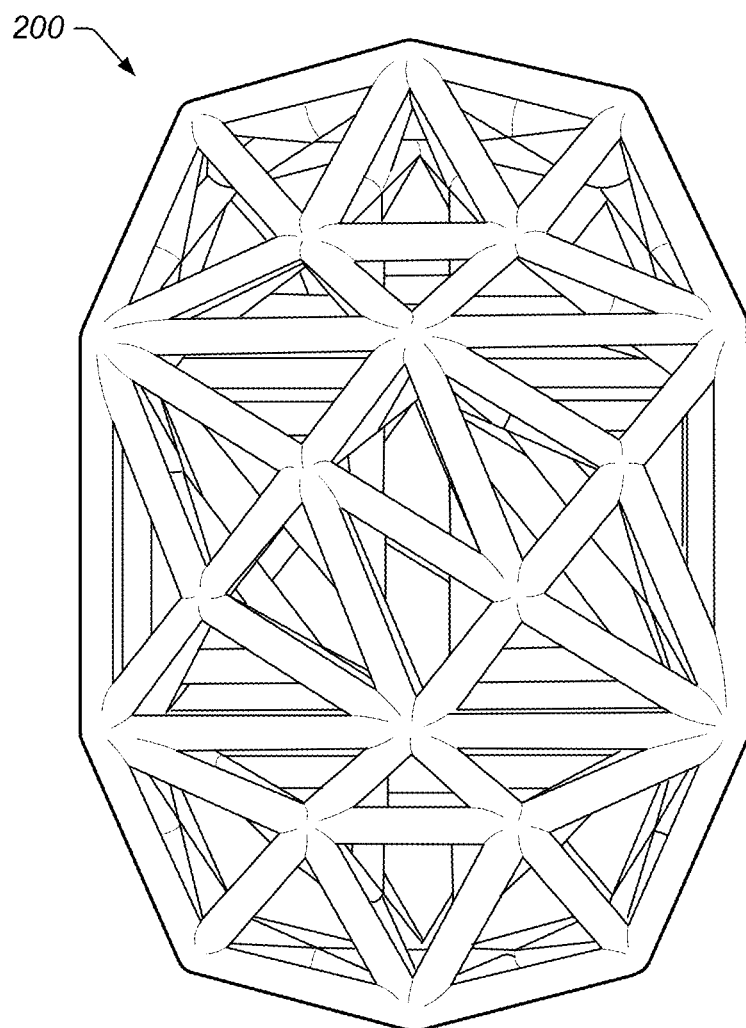
Figure 2C:
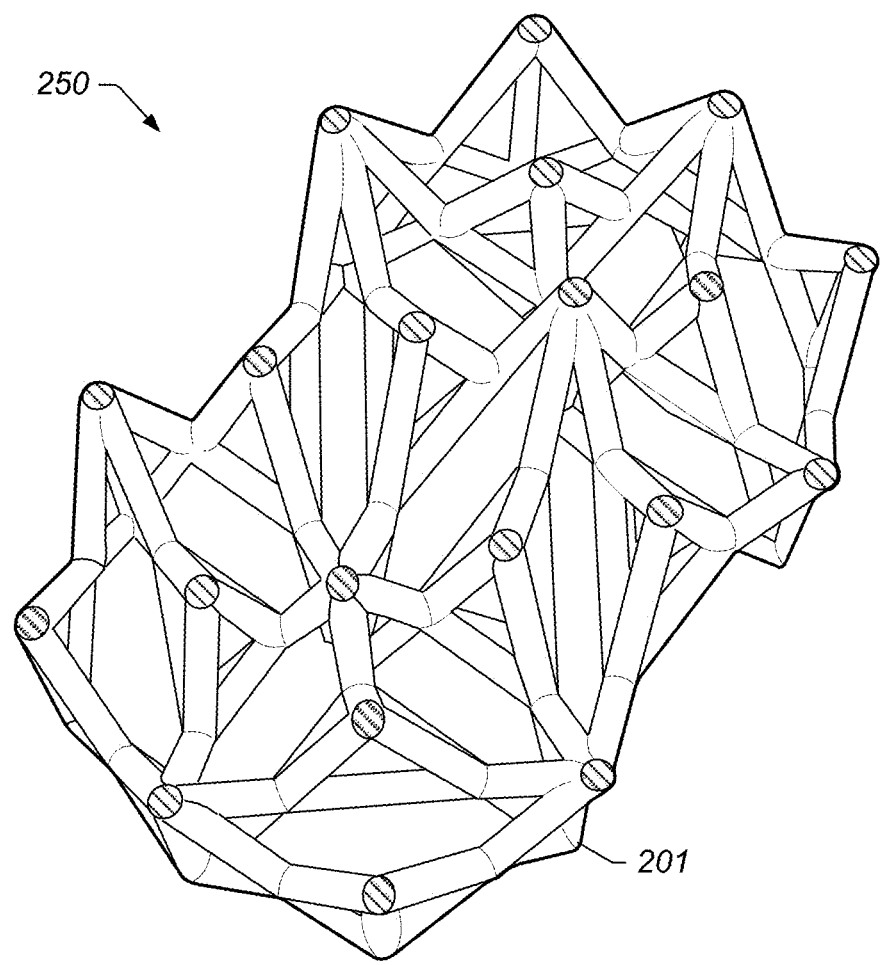

In one embodiment, the external truss portion may encompass the sides, top, and/or bottom of the implant. For example, in one embodiment, the external truss portion may include a top region, side regions, and/or a bottom region. FIG. 1A depicts an embodiment of implant 100 wherein external truss portion 105 includes a top 111, bottom 112 and a side region 113. As described above, side region 113 includes a series of planar trusses arranged vertically to form a circular/polygon ring-like structure that completely or at least partially surrounds the perimeter of the space truss disposed in the central portion of implant 100. In the depicted embodiment, top portion 111 of external truss structure 105 includes a plurality of truss units coupled to one another to form a planar truss that cover substantially all of the lop region of internal web structure 104. In the illustrated embodiment, the top portion 111 spans entirely the region between top edges of the side portion 113 of external truss structure 105. In the illustrated embodiment, top portion 111 is formed from a single planar truss that includes a plurality of truss units that lie in substantially the same plane. In other words, the planar truss of top portion 111 defines a generally flat surface. Although difficult to view in FIG. 1, the underside of implant 100 may include the bottom portion 112 having a configuration similar to that of the top portion 111. In other embodiments, external truss structure 105 may include a partial side, top and/or bottom external truss portions. Or may not include one or more of the side, top and bottom external truss portions. For example, as described in more detail below. FIG. 2C depicts an embodiment of implant 100 that includes an internal web structure formed from space trusses, that does not have an external truss structure.

In some embodiments, implant 100 may be formed from a biocompatible material such as a titanium alloy (e.g., γTitanium Aluminides), cobalt, chromium, stainless steel. Polyetheretherketone (PEEK), ceramics, etc. Other materials are also contemplated. In some embodiments, implant 100 may be made through a rapid prototyping process (e.g., electron beam melting (EBM) process) as further described below. Other processes are also possible (e.g., injection molding, casting, sintering, selective laser sintering (SLS), Direct Metal leaser Sintering (DMLS), etc). SLS may include laser-sintering of high-performance polymers such as that provided by EOS of North America. Inc., headquartered in Novi, Michigan, U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 11 provided by FDS of North America. Inc.

As described above, in some embodiments the web structure may be formed from a plurality of triangular planar truss units. In some embodiments, the planar truss units may be coupled to each other to define polyhedrons that define the internal web structure. Examples of polyhedron structures that may be created by joining planar truss units include, but are not limited to, tetrahedrons, pentahedrons, hexahedrons, heptahedrons, pyramids, octahedrons, dodecahedrons, icosahedrons, and spherical fullerenes. In some embodiments, such as those described above, the space truss of the web structure may connect multiple midpoints of tetrahedron building blocks and include a regular pattern of tetrahedron blocks arranged adjacent one another. In some embodiments, the web structure may not include a pattern of geometrical building blocks. Examples of implants composed of a web structure are described in U.S. Published Patent Applications Nos.: 2010/0161061; 2011/0196495; 20110313532; and 2013/0030529, each of which is incorporated herein by reference.

As shown in FIG. 1A, top surface 115a and bottom surface 115b of implant 100 may include triangles, squares, circles or other shapes (e.g., a random or custom design). Top and bottom surfaces 115a,b may be used to connect the top and bottom vertices of various geometrical building blocks used in the web structure of implant 100. For example, each vertex may be connected through struts to the neighboring vertices of other geometrical building blocks. Top surface 115a may include other strut networks and/or connections, in some embodiments, bottom surface 115b may mirror the top surface (and/or have other designs). In some embodiments, top surface 115a and bottom surface 115b may engage respective surfaces of two adjacent vertebrae when implant 100 is implanted.

As depicted in FIG. 1B, implant 100 may include lordosis (e.g., an angle in top and/or bottom surfaces 115a,b approximately in a range of 4 to 15 degrees (such as 4, 5, 6, 7, 8, 9, 10, 11, 12, 13, 14, or 15 degrees)) to further support the adjacent vertebrae when implanted. As described above, lordosis may include an angled orientation of surfaces (e.g., top and bottom) that provide for differences in thickness in the anterior and posterior portions of the implant such that the implant is conducive for supporting the curvature of a vertebral column. In the illustrated embodiment, the thickness of implant 100 is greater at or near the anterior portion 118 and lesser at or near the posterior portion 120 of the implant. In the illustrated embodiment, the side portions of external truss structure are arranged substantially vertically, and the lordosis is formed by the angles of the top portion 111 and bottom portion 112 of external truss structure, for example, in the illustrated embodiment, top portion 111 and bottom portion 112 of external truss structure are not perpendicular to the vertical plane defined by the side portion 113. Rather, the top portion 111 and bottom portion 112 are arranged with an acute angle relative to the vertical plane of side portion 113 at or near the anterior region 118 of implant 100 and with an obtuse angle relative to the vertical plane of side portion 113 at or near posterior region 120 of implant 100. As depicted, the vertical struts that form the planar truss of side portion 113 of external truss structure proximate posterior region 120 of implant 100 are shorter than struts that form side portion of external truss structure proximate anterior region 118 of implant 100. In the illustrated embodiment, in which the vertical trusses are substantially evenly spaced, the struts forming the "X" cross members of the side planar trusses proximate the posterior region 120 of implant 100 are shorter than struts forming the "X" cross members of the side planar trusses proximate the anterior region 118 of implant 100. Other embodiments may include variations in the arrangement of the trusses to provide various configurations of the implant. For example, in some embodiments only one or neither of the top and bottom external truss portions may be non-perpendicular to the side portions of the external truss proximate the anterior and posterior portions of the implant. Further, the side, top, and or bottom portions may include multiple planar trusses angled relative to one another in any orientation. For example, the top or bottom portions may include four planar trusses, each formed of multiple truss units, such that the portion(s) includes a pyramidal like shape.

Figure 2D:
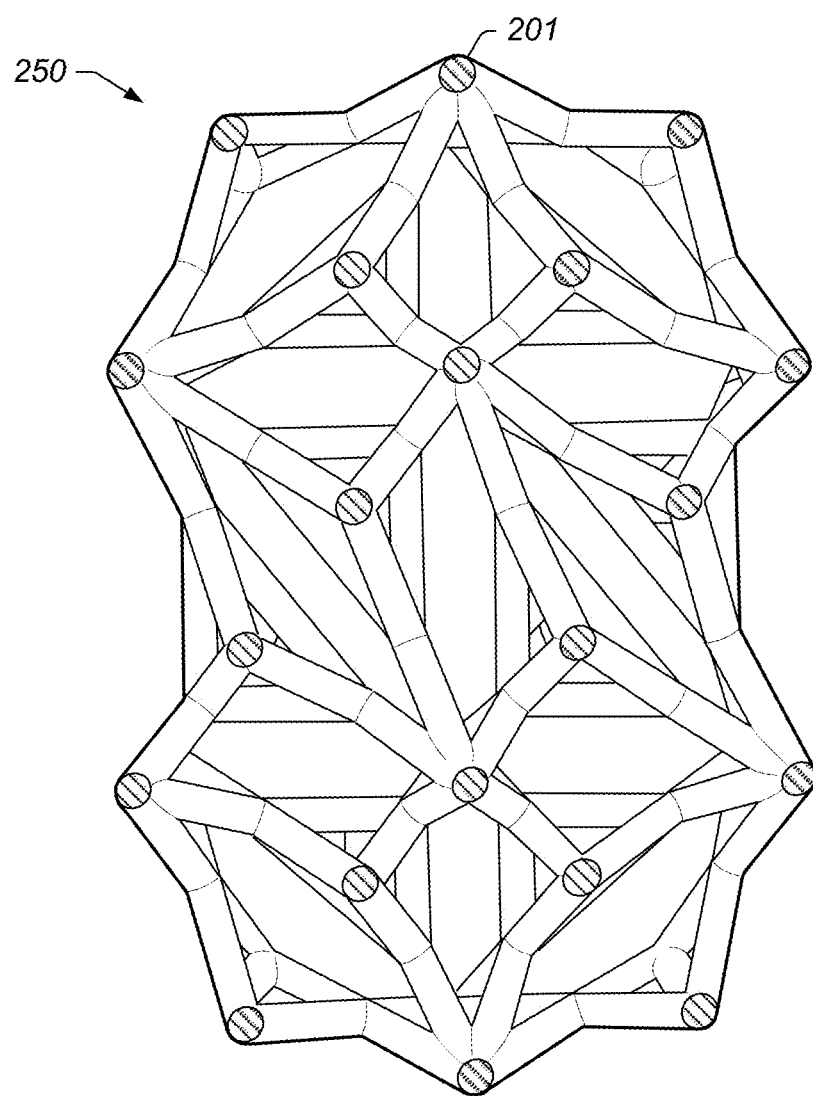

In some embodiments, the implant may not include lordosis. For example, FIGS. 2A-2B illustrate two views of an embodiment of an implant 200 without lordosis. In some embodiments, the top surface and bottom surface may not include connecting struts. For example, FIGS. 2C-2D illustrate two views of implant 250 without outer struts (e.g., without external truss portions formed of planar trusses). In the illustrated embodiment, implant 250 includes an internal web structure and does not include an external truss structure. For example, in the illustrated embodiment, the exterior faces of implant 250 are defined by a plurality of truss units that are angled relative to each of its adjacent truss units. The relative alignment of the truss units results in a non-planar exterior that includes a plurality of pointed junctions. The pointed junctions (e.g., pointed junction 201) may operate to dig into the surrounding bone to hold the implant in place (for example, if the implant is being used in a corpectomy device).

Figure 3A:
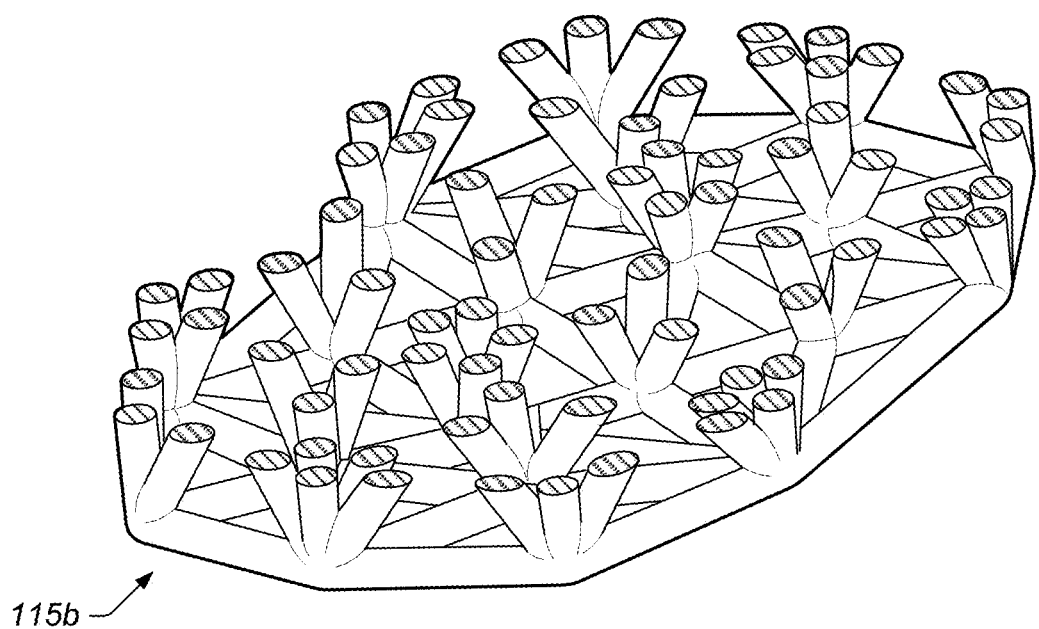
FIGS. 3A-3C illustrate progressive sectioned views of the implant showing the internal structure of the implant, according to an embodiment.
Figure 3B:
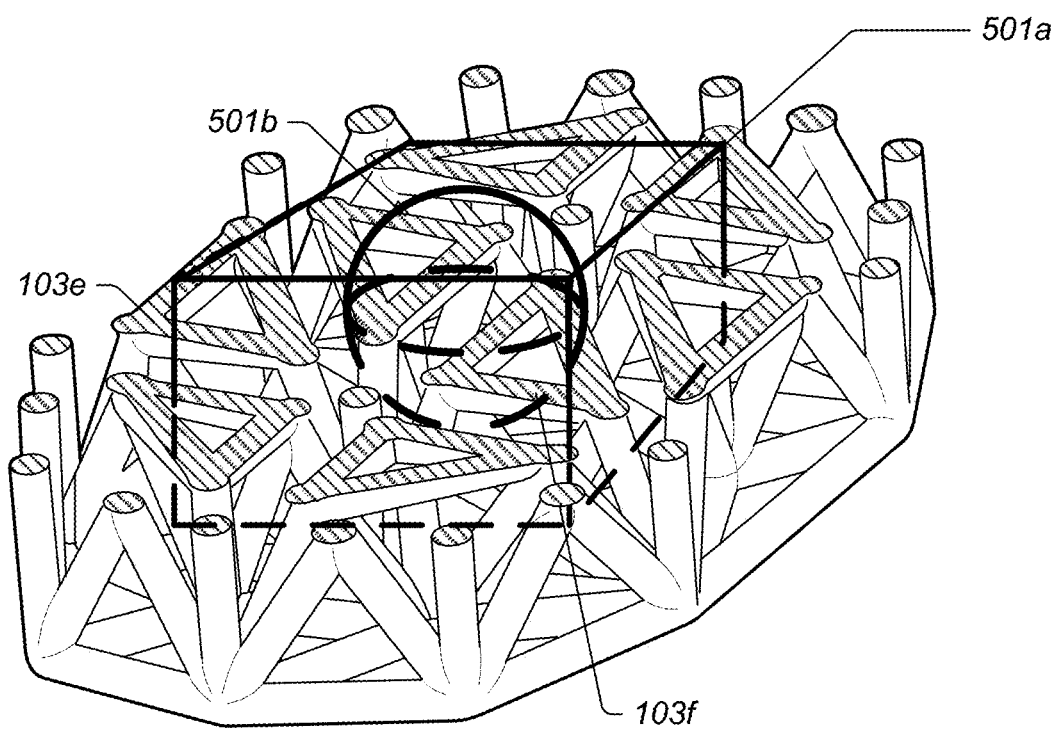
Figure 3C:
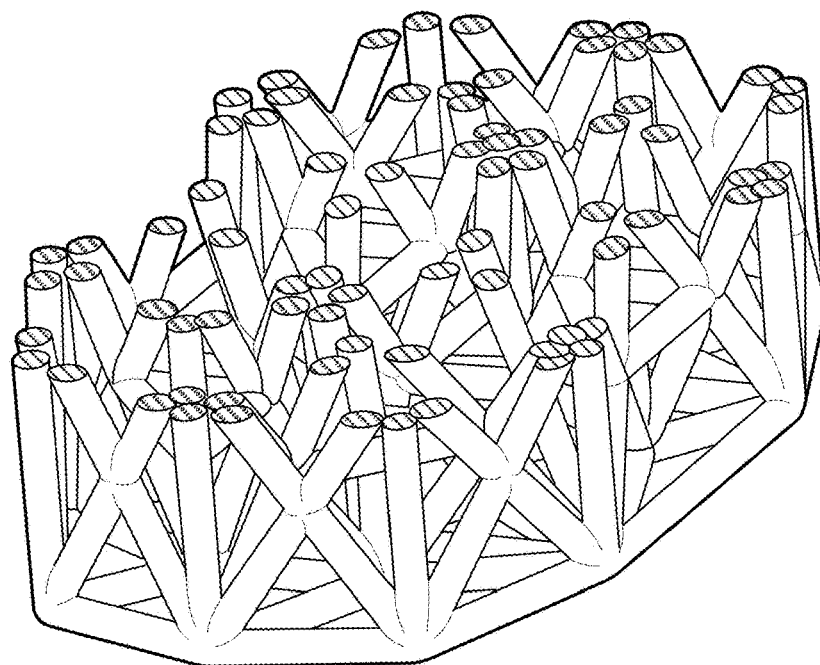
Figure 3D:
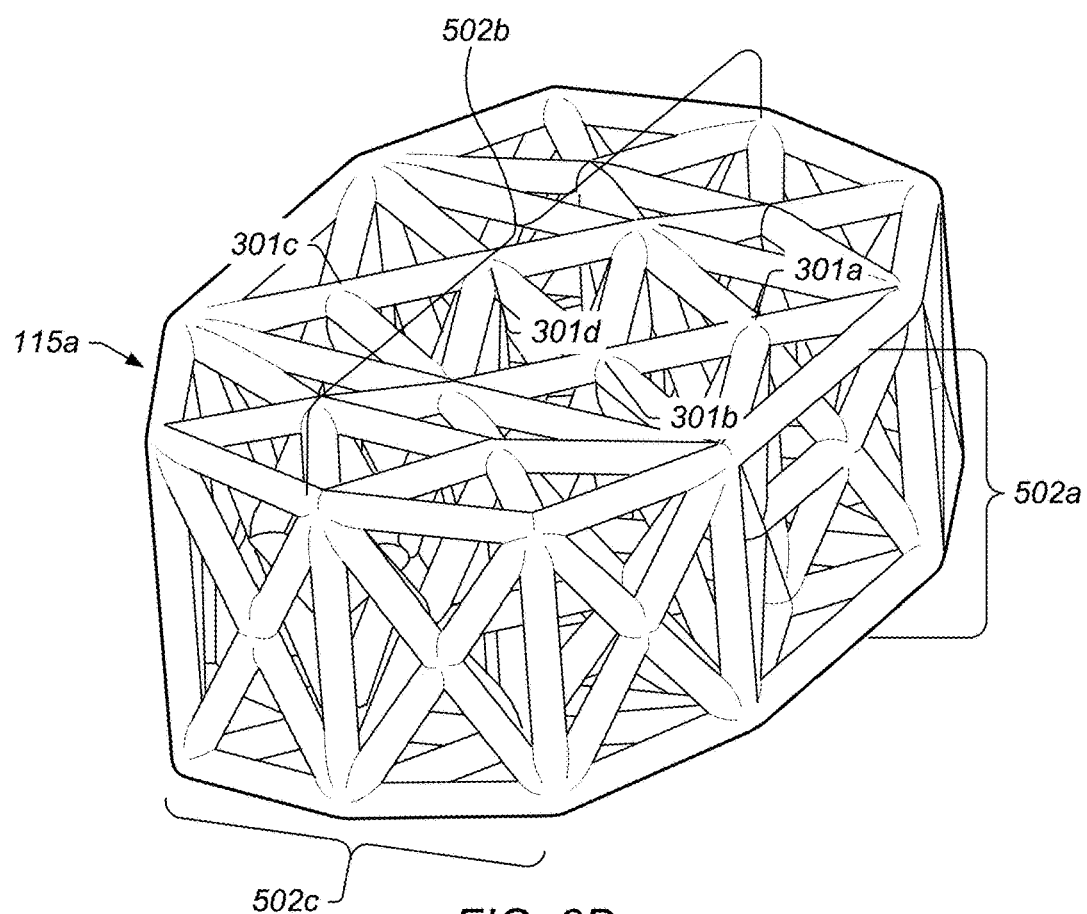
FIG. 3D illustrates an isometric view of the implant, according to an embodiment.

FIGS. 3A-3C illustrate progressive sectioned views of implant 100 showing the internal structure of implant 100, according to an embodiment. FIG. 3A illustrates a sectioned view of a lower portion of implant 100. Bottom surface 115b is shown with various struts (e.g., struts 103) extending upward from bottom surface 115b FIG. 3B illustrates a sectioned view approximately mid-way through implant 100. Struts, such as struts 103e,f, shared by various stacked tetrahedrons in the web structure are shown. Some struts extend through central portion 501a and/or 501b of implant 100 FIG. 3B also shows central portions 501a,b of implant 100. In some embodiments, central portion 501a may include a rectangular region that has a width of approximately 50% of the implant width, a height of approximately 50% of the implant height, and a length of approximately 50% of the implant length and located in the center of implant 100. In some embodiments, central portion 501b may encompass a region (e.g., a spherical region, square region, etc.) of approximately a radius of approximately ⅛ to ¼ of the width of implant 100 around a position located approximately at one half the width, approximately one half the length, and approximately one-half the height of implant 100 (i.e., the center of implant 100). Other central portions are also contemplated. For example, the central portion may include a square region with a length of one of the sides of the square region approximately ¼ to ½ the width of implant 100 around a position approximately at one half the width, approximately one half the length, and approximately one half the height of the implant. An example height 502a, width 502b, and length 502c, is shown in FIG. 3D. In some embodiments, the height may be up to about 75 mm or more. In some embodiments, such as those used for long bone reconstruction, the width and/or length could be approximately 7 inches or longer. In some embodiments, the width, length, and or height may vary along implant 100 (e.g., the height may vary if the implant includes lordosis). The height may be taken at one of the opposing sides, the middle, and/or may be an average of one or more heights along the length of implant 100. The web structure may extend through central portion 501a,b of the implant (e.g., at least one strut of the web structure may pass at least partially through central portion 501a,b). FIG. 3C illustrates another sectioned view showing sectioned views of top tetrahedrons in the web structure. FIG. 3D shows a complete view of implant 100 including top surface 115a with vertices 301a-d.

Figure 4A:
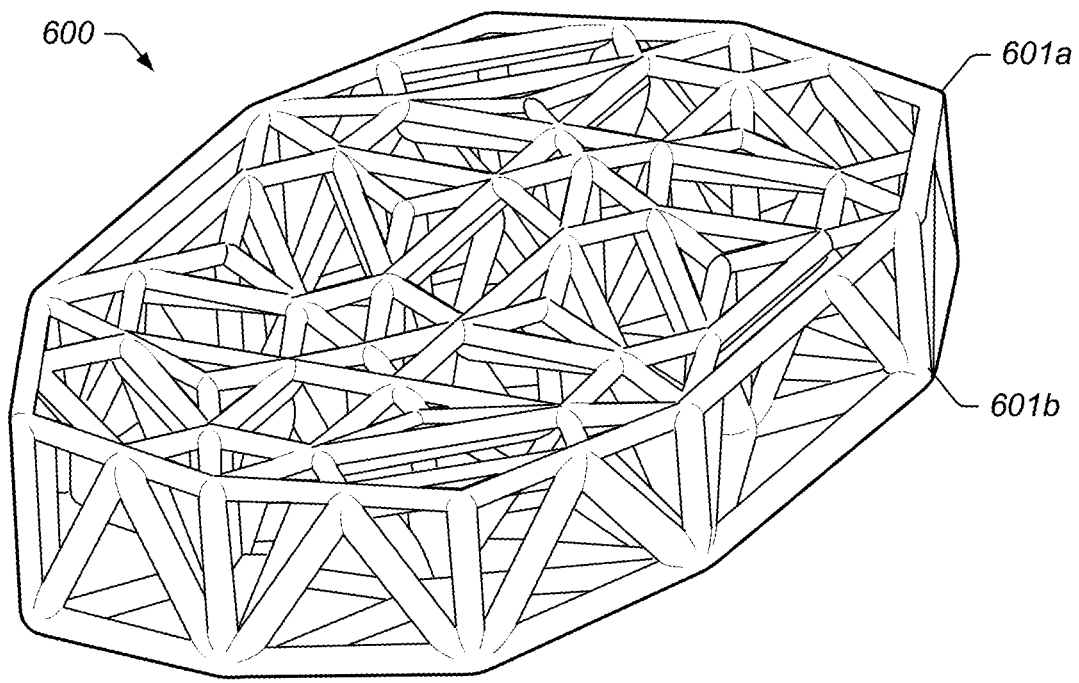
FIGS. 4A-4D illustrate another configuration of the web structure, according to an embodiment.
Figure 4B:
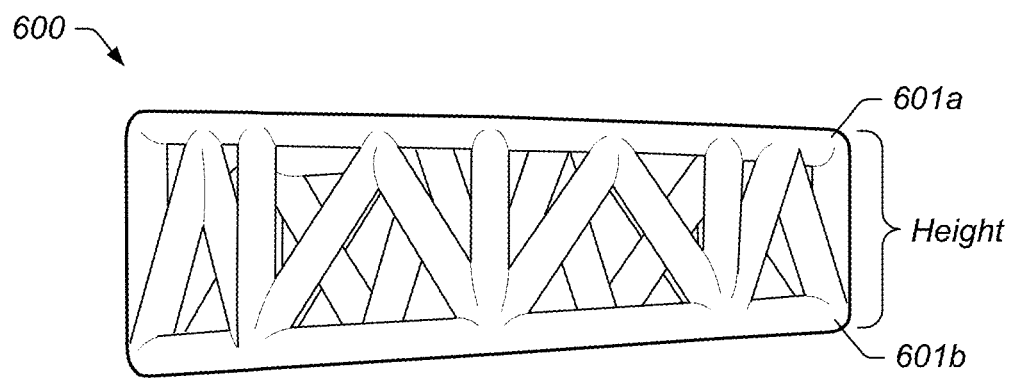

FIGS. 4A-4D illustrate alternate embodiments of an implant. In some embodiments, different sections of the hexahedron-shaped geometric design may be used. For example, as seen in FIG. 4A, the bottom half of the hexahedron-shaped geometric design may be used (primarily including the lower tetrahedron structures). If using the bottom half of the design, implant 600 may be expanded proportionately to have similar overall dimensions as the hexahedron-shaped geometric design (e.g., the tetrahedrons may be expanded to approximately twice the height of the tetrahedrons in the hexahedron-shaped geometric design to give implant 600 a height approximately the same as the hexahedron-shaped geometric design). In some embodiments, implant 600 may also be angled (e.g., on top surface 601a and or bottom surface 601b) to provide implant 600 with lordosis to, in some embodiments, have a better fit between the vertebral endplates. Top surface 601a and/or bottom surface 601b may also include struts to connect nodes of implant 600 (e.g., see the strut network on the top surface in FIG. 4A). Other patterns of struts for top surface 601a and/or bottom surface 601b may also be used. In some embodiments, implant 600 may not include negative angles between struts and may thus be easier to create through a casting or molding process.

Figure 4C:
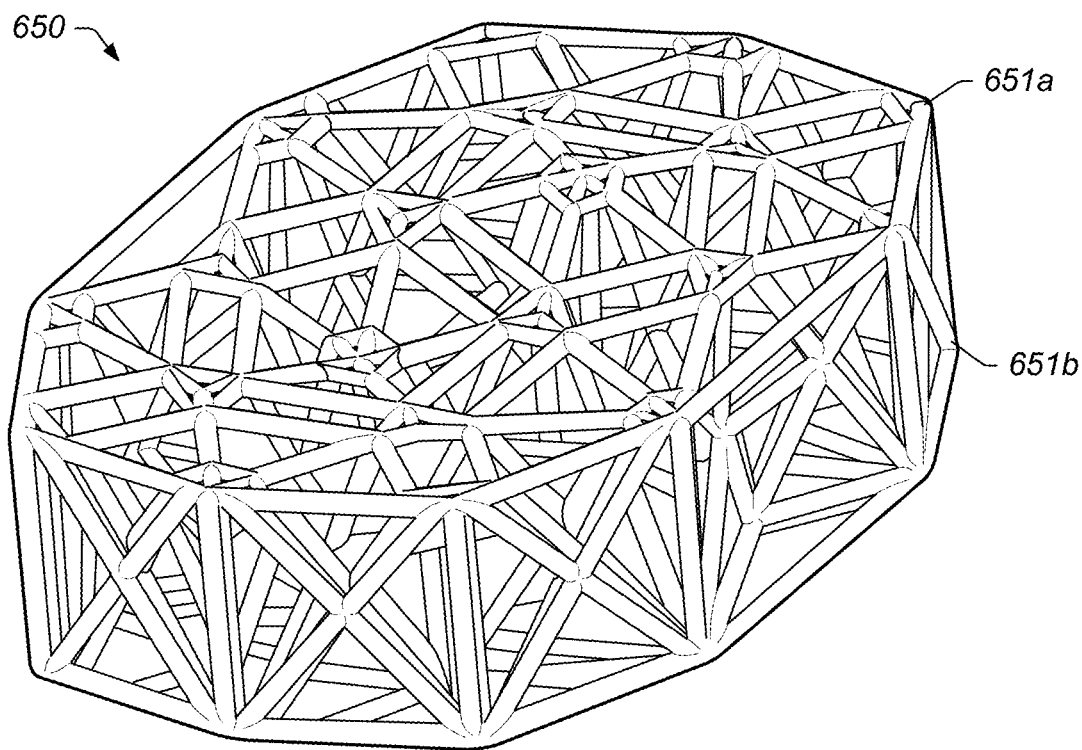
Figure 4D:
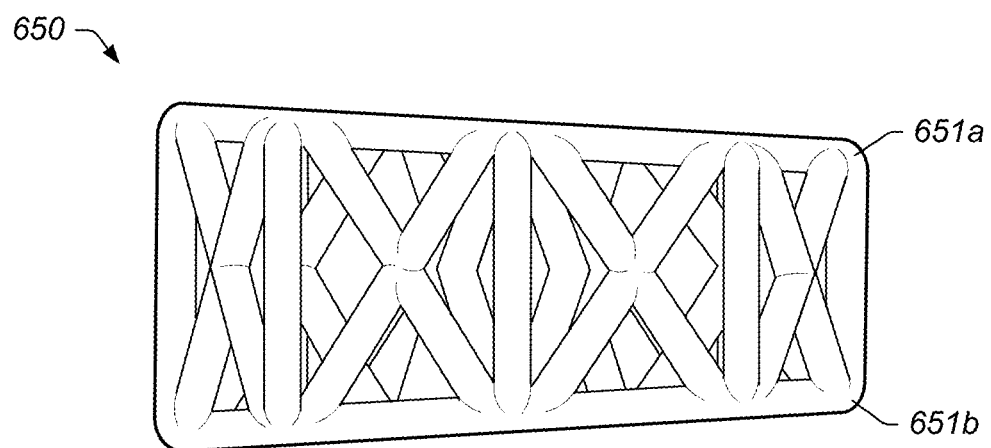

FIGS. 4C-4D illustrate another alternate embodiment of an implant. In some embodiments, approximately the middle 40 to 60 percent of the hexahedron-shaped geometric design may be used in implant 650. For example, if an overall height of the hexahedron-shaped geometric design is approximately 37 mm, approximately the bottom 10 mm and approximately the top 10 mm of the design may be removed and approximately the middle 17 mm of the design may be used for the implant. Middle portion of implant 650 may then be expanded proportionately such that the approximate height of the expanded design may be approximately 37 mm (or a different height as needed). Top surface 651a and bottom surface 651b may include a network of struts (e.g., see the struts on top surface 651a of FIG. 4C) (other networks of struts are also contemplated). Other portions of the design for the implant are also contemplated (e.g., the top half of the design shown in FIG. 1A, the bottom half of the design shown in FIG. 1A, etc). Design portions may be proportionately expanded to meet specified dimensions (e.g., specified height, width, and length). In some embodiments, the amount of struts may be reduced or material in the implant may be redistributed so that some struts may have a larger diameter and some may have a smaller diameter (e.g., the different diameters may reinforce against different directional forces). In some embodiments, a partial-design cage may be used (e.g., with half of the web structure so that the structure includes a tetrahedron. Further, in some embodiments, the implant may include angled surfaces (e.g., an angled top surface 651a and/or angled bottom surface 651b) to provide lordosis for implants to be implanted between the vertebral endplates.

In some embodiments, the web structure of an implant may distribute forces throughout the implant when implanted. For example, the connecting struts of the web structure may extend throughout the core of an implant, and the interconnectivity of struts may disperse the stress of compressive forces throughout implant to reduce the potential of stress risers (the distribution of forces throughout the implant may prevent concentration of stress on one or more portions of the vertebrae that may otherwise result in damage to the vertebrae).

In some embodiments, the web structure of an implant (e.g., the external and internal struts of the implant) may also provide surface area for bone graft fusion. For example, the web structure extending throughout an implant may add additional surface areas (e.g., on the surface of the struts making up the implant) to fuse to the bone graft material and prevent bone graft material from loosening or migrating from the implant. In some embodiments, the web structure may also support bone in-growth. For example, when implanted, adjacent bone (e.g., adjacent vertebrae if the implant is used as a spinal implant) may grow over at least a portion of struts of the implant. The bone growth and engagement between the bone growth and the implant may further stabilize the implant. In some embodiments, the surfaces of the implant may be formed with a rough surface to assist in bone in-growth adhesion.

In some embodiments, struts may have a diameter approximately in a range of about 0.025 to 5 millimeters (mm) (e.g., 1.0 mm, 1.5 mm, 3 mm, etc). Other diameters are also contemplated (e.g., greater than 5 mm). In some embodiments, the struts may have a length approximately in a range of 0.5 to 20 mm (e.g., depending on the implant size needed to, for example, fit a gap between vertebral endplates). As another example, struts may have a length approximately in a range of 30-40 mm for a hip implant. In some embodiments, the reduced strut size of the web structure may allow the open cells in implant 100 to facilitate bone growth (e.g., bone may grow through the open cells once implant 100 is implanted in the body). Average subsidence for implants may be approximately 1.5 mm within the first 3 weeks post op (other subsidence is also possible (e.g., approximately between 0.5 to 2.5 mm)). A strut size that approximately matches the subsidence (e.g., a strut size of approximately 1.5 mm in diameter and a subsidence of approximately 1.5 mm) may result in a net 0 impedance (e.g., the bone growth growing around the struts) after the implant has settled in the implanted position. The net 0 impedance throughout the entire surface area of the implant/vertebrae endplate interface may result in a larger fusion column of bone that may result in more stable fusion. Other fusion column sizes are also contemplated. The configuration of the implant may redistribute the metal throughout the implant. In some embodiments, a rim may not be included on the implant (in some embodiments, a rim may be included). The resulting bone growth (e.g., spinal column) may grow through the implant.

In some embodiments, greater than 50% of the interior volume of implant 100 may be open. In some embodiments, greater than 60%, greater than 70%, and/or greater than 80% of implant 100 may be open (e.g., 95%). In some embodiments, the open volume may be filled with bone graft material. For example, cancellous bone may be packed into an open/internal region of implant.

As the implant settles into the implant site, subsidence may place additional pressure on the bone graft material (which may already be under compressive forces in the implant) and act to push the bone graft material toward the sides of the implant (according to Boussinesq's theory of adjacent material, when a force is applied to a member that is adjacent to other materials (such as sand, dirt, or bone graft material) the force against the member creates a zone of increased pressure (e.g., 60 degrees) in the adjacent material). Struts of the implant may resist bone graft material protrusion from the sides of the web structure and may increase the pressure of the bone graft material. Bone graft material may need to be implanted in a higher-pressure environment to create an environment conducive to strong bone growth (e.g., according to Wolfs law that bone in a healthy person or animal will adapt to the loads it is placed under). The web structure may thus increase the chance of stronger fusion.

Web structures formed from other truss configurations are also contemplated. For example, the trusses may include a series of packing triangles, a two-web truss, a three-web truss, etc. Further, the web structure for an implant may include one or more trusses as described in U.S. Pat. No. 6,931,812 titled "Web Structure and Method For Making the Same", which issued Aug. 23, 2005, which is hereby incorporated by reference in its entirety as though fully and completely set forth herein.

Figure 5:
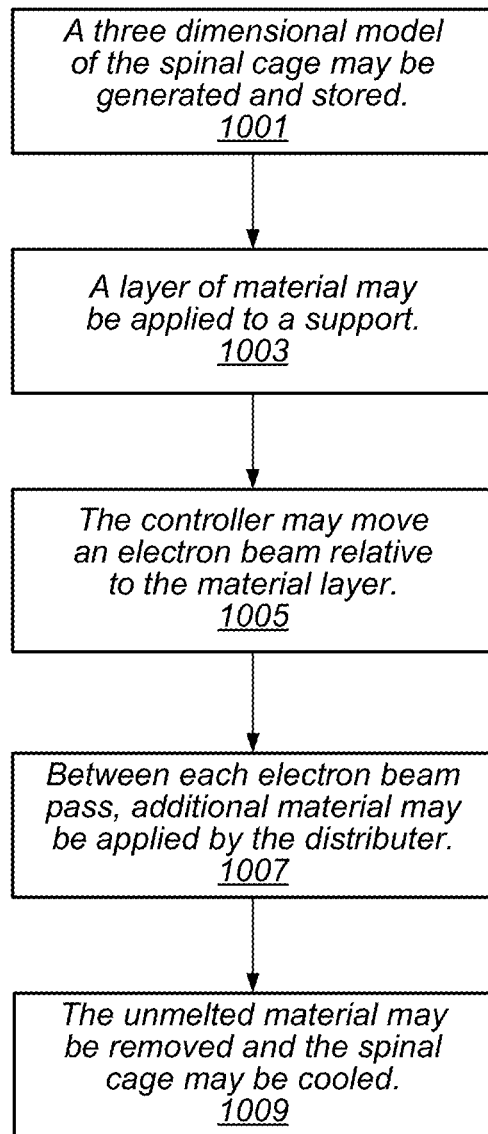
FIG. 5 illustrates a flowchart of a method for making an implant, according to an embodiment.

FIG. 5 illustrates a flowchart of a method for making an implant. In some embodiments, an implant may be made through rapid prototyping (e.g., electron beam melting, laser sintering, etc). It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At 1001, a three-dimensional model of an implant is generated and stored in a storage medium accessible to a controller operable to control the implant production process. At 1003, a layer of material (e.g., a powder, liquid, etc.) is applied to a support. In some embodiments, the powder may include γTiAl (γTitanium Alum in ides) which may be a high strength/low weight material. Other materials may also be used. The powder may be formed using a gas atomization process and may include granules with diameters approximately in a range of 20 to 200 micrometers (μm) (e.g., approximately 80 μm). The powder may be delivered to the support through a distributer (e.g., delivered from a storage container). The distributer and/or the support may move during distribution to apply a layer (e.g., of powder) to the support. In some embodiments, the layer may be approximately a uniform thickness (e.g., with an average thickness of 20 to 200 micrometers (μm)). In some embodiments, the distributer and support may not move (e.g., the material may be sprayed onto the support). At 1005, the controller moves an electron beam relative to the material layer. In some embodiments, the electron beam generator may be moved, and in some embodiments the support may be moved. If the material is γTiAl, a melting temperature approximately in a range of 1200 to 1800 degrees Celsius (e.g., 1500 degrees Celsius) may be obtained between the electron beam and the material. At 1007, between each electron beam pass, additional material may be applied by the distributer. At 1009, the unmelted material is removed and the implantcooled (e.g., using a cool inert gas). In some embodiments, the edges of the implant may be smoothed to remove rough edges (e.g., using a diamond sander). In some embodiments, the implant may include rough edges to increase friction between the implant and the surrounding bone to increase adhesion of the implant to the bone.

Other methods of making an implant are also contemplated. For example, an implant may be cast or injection molded. In some embodiments, multiple pans may be cast or injection molded and joined together (e.g., through welding, melting, etc). In some embodiments, individual struts forming the implant may be generated separately (e.g., by casting, injection molding, etc.) and welded together to form the implant. In some embodiments, multiple implants of different sizes may be constructed and delivered in a kit. A medical health professional may choose an implant (e.g., according to a needed size) during the surgery. In some embodiments, multiple implants may be used at the implant site.

Specialized tools may be used to insert the implants described herein. Examples of tools that may be used are described in U.S. Published Patent Applications Nos.: 2010/0161061; 2011/0196495; 20110313532; and 2013/0030529, each of which is incorporated herein by reference.

Figure 6:
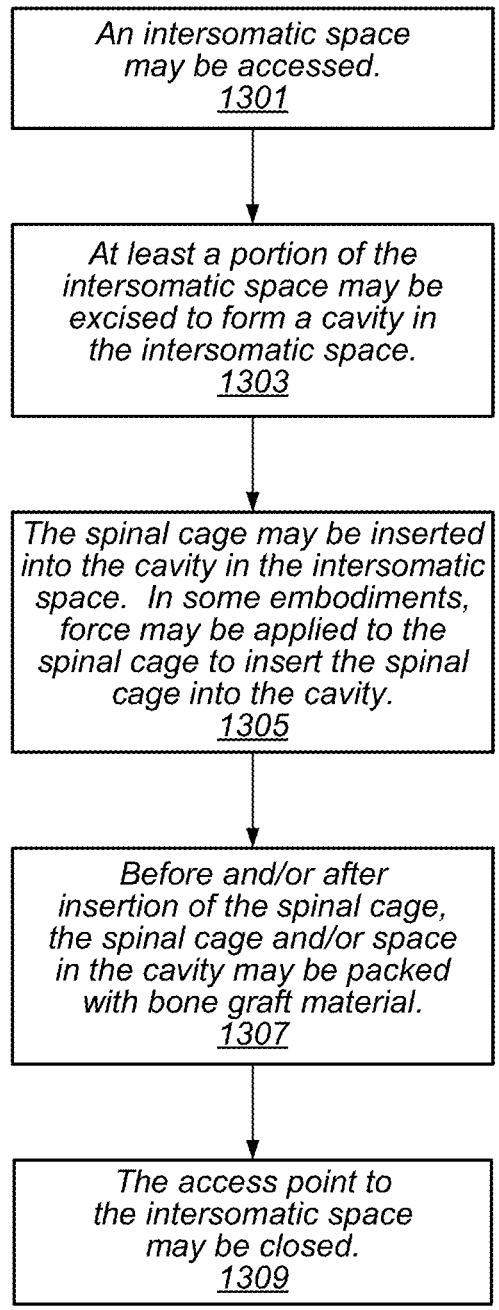
FIG. 6 illustrates a flowchart of a method for implanting a spinal implant, according to an embodiment.

FIG. 6 illustrates a flowchart of a method for implanting a spinal implant, according to an embodiment. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At step 1301, an intersomatic space is accessed. For example, an anterior opening may be made in a patient's body for an anterior lumbar inter-body fusion (ALIF) approach or a posterior opening may be made for a posterior lumbar inter-body fusion (PLIF) approach. At 1303, at least a portion of the intersomatic space is excised to form a cavity in the intersomatic space. At 1305, the implant is inserted into the cavity in the intersomatic space. In some embodiments, a handler, or some other device, is used to grip the implant. In some embodiments, a force may be applied to the implant (e.g., through a hammer) to insert the implant into the cavity. At 1307, before and/or after insertion of the implant, the implant and/or space in the cavity may be packed with bone graft material. At 1309, the access point to the intersomatic space may be closed (e.g., using sutures).

In some embodiments, the implant may be customized. For example, three dimensional measurements and/or shape of the implant may be used to construct an implant that distributes the web structure throughout a three-dimensional shape design.

In some embodiments, a truss/web structure may be disposed on at least a portion of an implant to facilitate coupling of the implant to an adjacent structure. For example, where an implant is implanted adjacent a bony structure, one or more truss structures may be disposed on and/or extend from a surface (e.g., an interface plate) of the implant that is intended to contact, and at least partially adhere to, the bony structure during use. In some embodiments, such as those including an intervertebral implant disposed between the end plates of two adjacent vertebrae during, one or more truss structures may be disposed on a contact surface of the intervertebral implant to facilitate bone growth that enhances coupling of the intervertebral implant to the bony structure. For example, a truss structure may include one or more struts that extend from the contact surface to define an open space for bone growth therethrough, thereby enabling bone through growth to interlock the bone structure and the truss structure with one another to couple the implant to the bony structure at or near the contact face. Such interlocking bone through growth may inhibit movement between the implant and the bony structure which could otherwise lead to loosening, migration, subsidence, or dislodging of the implant from the intended position. Similar techniques may be employed with various types of implants, including those intended to interface with tissue and/or bone structures. For example, a truss structure may be employed on a contact surface of knee implants, in a corpectomy device, in a hip replacement, in a knee replacement, in a long bone reconstruction scaffold, or in a cranio-maxifacial implant hip implants, jaw implant, an implant for long bone reconstruction, foot and ankle implants, shoulder implants or other joint replacement implants or the like to enhance adherence of the implant to the adjacent bony structure or tissue. Examples of truss structures, and other structures, that may extend from the surface of an implant to facilitate coupling of the implant to an adjacent structure are described in U.S. Published Patent Application No. 2011/0313532, which is incorporated herein by reference.

While implants described herein are depicted as being composed of substantially straight struts, it should be understood that the struts can be non-linear, including, but not limited to curved, arcuate and arch shaped. Examples of implants having non-linear struts are described in U.S. patent application Ser. No. 13/668,968, which is incorporated herein by reference.

It is known that osteoblasts under an appropriate load produce bone morphogenetic protein ("BMP"). BMPs are a group of growth factors also known as cytokines and as metabologens. BMPs act as morphogenetic signals that signal the formation of bone (i.e., an osteogenetic response). Thus, by increasing the production of one or more BMPs the osteogentic response to an implant is increased, creating an implant that is integrated into the newly formed bone.

Figure 7:
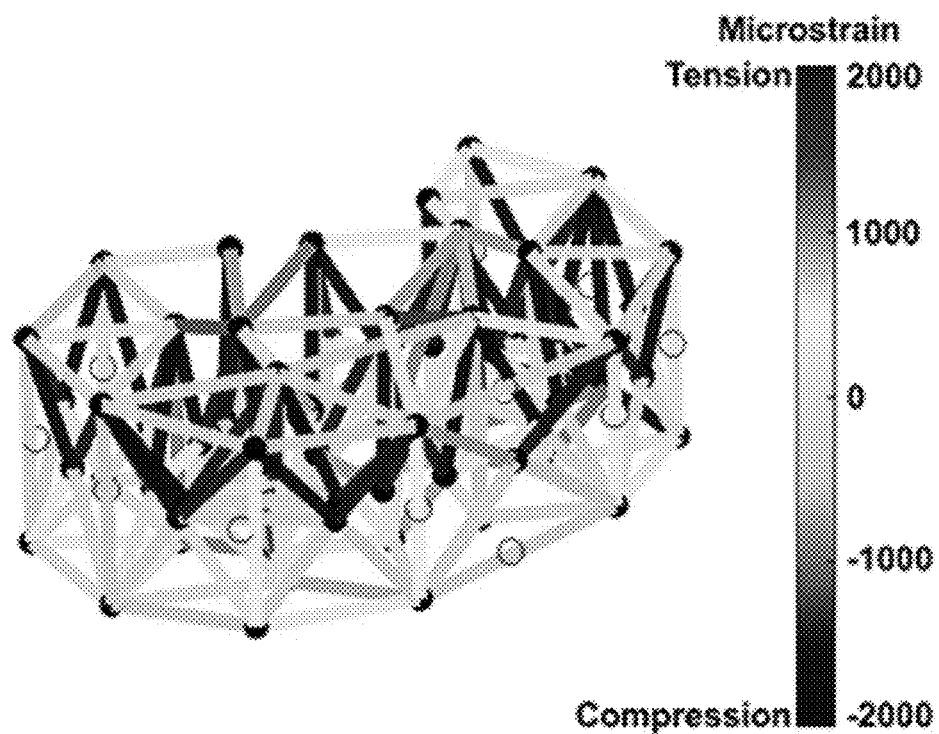
FIG. 7 depicts a diagram of stresses distributed through an implant.
Figure 8A:
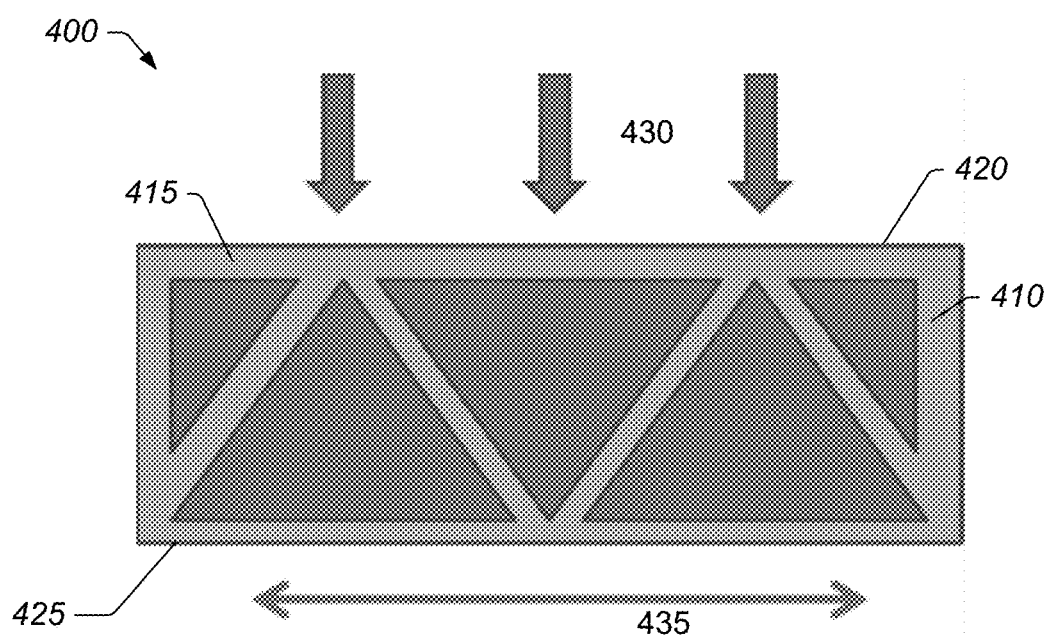
FIGS. 8A-C depict schematic diagrams of the effect of compression on osteoblast cells.
Figure 8B:
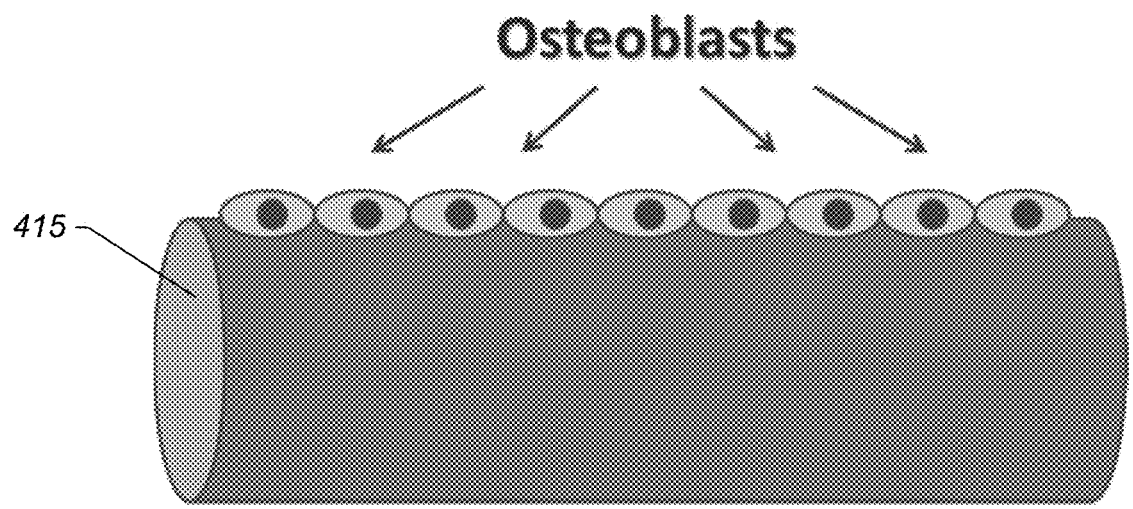
Figure 8C:
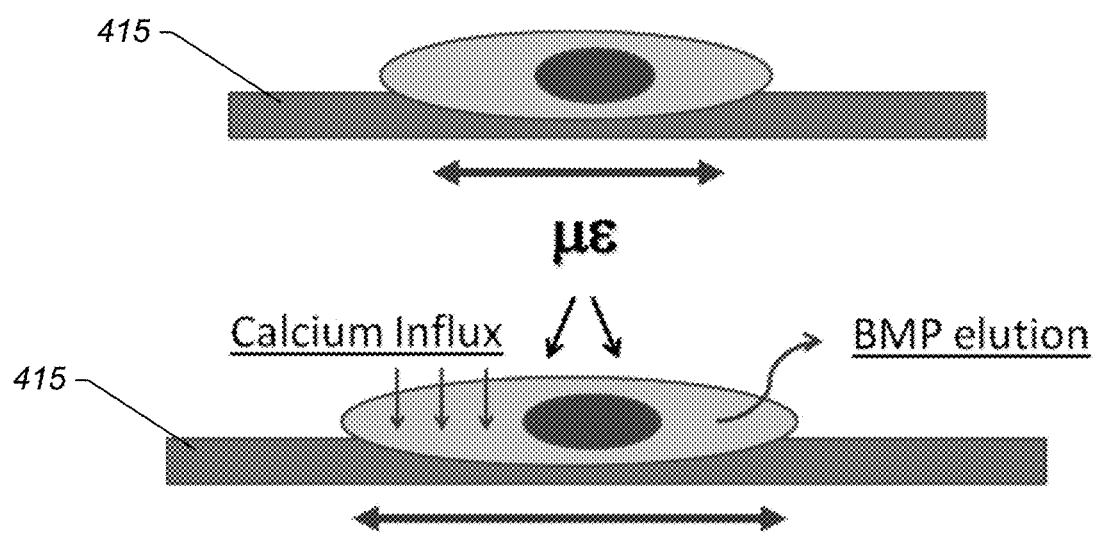

A web structure that includes a plurality of joined truss units exhibits a number of deformations in response to loading. FIG. 7 below depicts some of the forces that are dispersed along the struts of the truss units that make up the web structure. When used as a bone implant, web structures as described herein may promote the growth of bone in and around the web structure, in part, because of the enhanced BMP production. As shown in FIGS. 8A-C, osteoblasts become attached to the struts of a web structure. Under loading, the micro strain in the struts causes localized deformation which in turn transfers the strain to the adhered osteoblasts which cause the osteoblasts to elute BMP.

FIG. 8A depicts a schematic diagram of an implant 400 that includes a space truss 410. Bone structures, not shown, are typically disposed against a top face 420 and a bottom face 425 of implant 400. During use, the stress from the contacting bone structures (denoted by arrows 430) can cause implant 400 to lengthen (denoted by arrow 435) as the implant is compressed. This lengthening can have a beneficial effect on the formation of BMP by osteoblasts that adhere to the implant. Adjacent bone adds compression forces to the slanted struts. This compression may lead to bone remodeling. The combination of the two forces (compression and lengthening) creates bone growth/remodeling which leads to accelerated healing and achieving a mature fusion in a shorter amount of time as compared to predicate devices.

FIG. 8B depicts a close-up view of strut 415 of implant 400. Strut 415, in FIG. 8B is shown in a non-elongated state. This may represent the state of strut 415 when the implant is not under load from the contacting bone structures. Osteoblasts are depicted as adhered to strut 415. The osteoblasts are shown in their normal, non-elongated form. FIG. 8C depicts strut 415 in an elongated state, which exists when the bone structures are applying a compressive force to implant 400. As shown, the osteoblasts are believed to be stretched due to the elongation of strut 415. Elongation of the osteoblasts lead to an influx of calcium which is then converted into BMP and eluted back out. Studies have shown that the creating a microstrain in the osteoblasts of between 500µε and 2000µε or between about 1000µε and about 1500µε enhances the production of BMP. Alternatively, the production of BMP may be attained when the length of the attached osteoblasts is changed between about 0.05% and about 0.2% or between about 0.1% and about 0.15%. Configuring a truss system to intentionally create lengthening/microstrain in osteoblasts may reduce the time needed for the bone structure to be repaired.

In an embodiment, an implant for interfacing with a bone structure includes a web structure comprising a plurality of struts joined at nodes. The web structure is configured to interface with human hone tissue. In one embodiment, a diameter and/or length of the struts are predetermined such that when the web structure is in contact with the bone structure, BMP production from osteoblasts adhering to the implant surface is achieved. In one embodiment, the diameter and/or length of the struts is predetermined so that at least a portion of the struts create a microstrain in the adhered osteoblasts of between about 1 and 5000 microstrain, 500µε and about 2000µε or between about 1000µε and about 1500µε. In an embodiment, the diameter and/or length of the struts is predetermined so that at least a portion of the struts create a change in length of the adhered osteoblasts of between about 0.05% and about 0.2% or between about 0.1% and about 0.15%.

An implant may be prepared having struts of a length of between about 1 to 100 mm. The diameter of the struts may be set such that the strut undergoes a change of length of between about 0.05% and 0.2% when the web structure is in contact with the bone structure. In some embodiments, the diameter of the struts is predetermined such that the strut undergoes a change of length of between about 0.000125% and 0.0005% or between about 0.00025% and 0.000375%.

Any implant described herein may be modified so that at least a portion of the struts the form the web structure produce the appropriate microstrain lengthening of adhered osteoblasts. In some embodiments, most if not all of the struts that form the web structure of an implant may be 'programmed' (or designed) to stimulate BMP production. In other embodiments, some struts may be programmed designed for BMP production, while other struts have different physical properties than the programmed struts.

An implant may be optimized to distribute stresses encountered by the implant. Most implants used for bone repair are placed in locations that apply non-uniform stress to the implant. The non-uniform stress creates different forces across the implant. If an implant is designed to withstand a certain homogenous force, the implant may fail when subjected to non-uniform stress. In a non-uniform stress situation, some of the stress on the implant may be sufficient to deform the implant. It is desirable to have an implant that is customized to the expected non-uniform stress that will be encountered in the bone structure being repaired.

In an embodiment, an implant for interfacing with a bone structure, includes a web structure having a plurality of struts joined at nodes. The web structure is configured to interface with human bone tissue, and has a first bone contact surface and a second bone contact surface. A first portion of struts that are part of the space truss have a physical property that is different from a second portion of the struts that are a pan of the space truss. In this manner an implant may be created which optimizes the stresses encountered by the implant to help inhibit failure of the implant.

In one embodiment, the first portion cf struts that are part of the space truss have a deformation strength that is different from a second port ion of the struts that are a part of the space truss. The space truss may include one or more central struts extending from the first bone contact surface to the second bone contact surface. The central struts may have a deformation strength that is greater than or less than the surrounding struts, depending on the location of the implant. The space truss may include one or more longitudinal struts extending parallel to the first bone contact surface and/cur the second bone contact surface, wherein the longitudinal struts have a deformation strength that is greater than or less than the surrounding struts.

The physical properties of the struts of the implant may be varied such that the diameter of the first portion of the struts is greater than a diameter of the second portion of the struts In some embodiments, the first portion of struts are formed from a material that is different from the material used to form the second portion of struts. In some embodiments, the first portion of struts have a diameter that is different from the diameter of the second portion of struts. In some embodiments, the first portion of struts have a density that is different from the density of the second portion of struts. In some embodiments, the first portion of struts have a porosity that is different from the porosity of the second portion of struts. Any combination of these different physical properties may be present in an implant to help optimize the distribution of stress throughout the implant.

Bone Growth Promoting Fibers and Particles

In various embodiments, one or more biologies (or bone growth factors) may be included in an implant. For instance, various biologics may be included to promote bone growth or bone adhesion, or to add an antimicrobial agent to prevent infections, fan some embodiments, biologies are added to an implant by coating structures (e.g., struts) of the implant with fibers and/or particles. In some embodiments, biologies are added to an implant by placing or positioning fibers and/or particles inside the interior volume (e.g., open space) of the implant. For example, the fibers or particles may fill at least a portion of an interior volume of the implant. Embodiments may also be contemplated with combinations of coating fibers and or particles or filling the interior volume with fibers or particles. Such combinations may include the same types of fibers or particles as both coatings and fillings or different types of fibers or particles for the coatings and fillings.

In some embodiments, a biologic may include a coating, such as hydroxyapatite, bone morphogenetic protein (BMP), insulin-like growth factors I and II, transforming growth factor-beta, acidic and basic fibroblast growth factor, platelet-derived growth factor, and/or similar bone growth stimulant that facilitates good biological fixation between the bone growth and a surface of the implant. In some embodiments, a bone growth factor may include a naturally occurring substance capable of stimulating cellular growth, proliferation and cellular differentiation (e.g., a protein or steroid hormone). In some embodiments, the surface of the implant (e.g., the struts, the external truss structure, etc.) may be coated with collagen (e.g., collagen fibers or particles).

In some embodiments, a biologic and/or growth factor may be secured to a central region of an implant. For example, in some embodiments, a biologic or growth factor may be provided on at least a portion of a strut that extends through central portion 501*a* and/or 501*b* of implant 100, shown in FIG. 3B. Such an embodiment may enable the delivery of a biologic and or a growth factor to a central portion of an implant. For example, the biologic or growth factor may be physically secured to a strut in a central portion of the implant as opposed to being packed into an open volume that does not include a strut provided therein for the physical attachment of the biologic and/or growth factor.

In some embodiments, implants may be at least partially filled or coated with nanofibers and/or microfibers that include a bone promoting agent. The term "microfiber" refers to fibers whose diameter ranges from about I micrometer to about 1000 micrometers The term "nanofiber" refers to fibers whose diameter ranges from about 1 nanometer to about 1000 nanometers. The term "macrofibers" refers to fibers whose diameters are above about 1000 micrometers. As used herein, the term "fibers" without a qualifier, refers to macrofibers, millimeter fibers, microfibers, and nanofibers.

Examples of bone growth promoting agents include, but are not limited to, calcium phosphate materials, biological bone growth promoting agents, and polysaccharides. Examples of calcium phosphate materials include, but are not limited to, hydroxyapatite (Hap, $Ca_{10}(PO_4)_6(OH)_2$), $\alpha$- and $\beta$-tricalcium phosphate (TCP; $Ca_3(PO_4)_2$), and whitloekite (WH, $Ca_9Mg(HPO_4)(PO_4)_6$).

Biological bone promoting agents include, but are not limited to, proteins, peptides, and small organic molecules that promote or enhance bone growth. Promotion or enhancement of bone growth may, in some embodiments, be accomplished by increasing the concentration of bone promoting proteins either directly or indirectly. Direct promotion of bone growth may be accomplished by treating a site in need of bone repair with a protein or peptide that creates a bone growth promoting response. Examples of agents that directly promote bone growth include, but are not limited to, insulin-like growth factor (IGF-I, IGF-II), transforming growth factor $\beta$ (TGF$\beta$), heparin binding growth. Factor (HBGF), stromal cell-derived factor (SDF-1), vascular endothelial growth factor (VEGF), fibroblast growth factor (FGF), platelet-derived growth factor (PDGF), parathyroid hormone (PTH), parathyroid hormone Related peptide (PTHrP), basic fibroblast growth factor (bFGF); TGF$\beta$ superfamily factor; bone morphogenetic protein (BMP), preferably BMP2, BMP3, BMP4, BMP5, BMP7, somatropin, growth differentiation factor (GDF), bone-specific alkaline phosphatase (BAP), collagen, osteocalch (bone gamma-carboxyglutamic acid-containing protein (BGLAP)), granulocyte colony-stimulating factor (GCSF), phosphate-regulating neutral endopeptidase, X-linked (PHEX), and transcription factor Sp7 (SP7). Agents that indirectly promote bone growth trigger the body to produce direct bone promoting agents in response to the indirect bone growth promoting agent.

Polysaccharides include, but are not limited to dextran, agar, alginic acid, hyaluronic acid, imtlin, pullulan, heparin, fucoidan, chitcsan, scleroglucan, curdlan, starch, cellulose, and the like. Additionally, chemically modified polysaccharides with acidic groups (carboxylates, sulfates, phosphates), amino groups (ethyleneamine, thethylaminoethylamine, propylamine), and hydrophobic groups (alkyl, benzyl) may be used.

In various embodiments, fibers that include a bone growth promoting agent may be produced by an electrospinning process. The electrospinning process applies a high voltage to a polymer solution or melt as the material is ejected through a needle. The electric voltage is sufficient enough to overcome the surface tension of the polymer solution or melt and causes the polymer droplets to elongate so that the polymer is pulled into fibers. The fibers are collected on a grounded or charged metal plate in the form of non-woven mats.

In an alternative embodiment, fibers that include a bone growth promoting agent may be produced by a centrifugal spinning process. In a centrifugal spinning process, a polymer solution or melt is loaded into a "spinneret." The spinneret is then rotated at speeds (typically at least 500 rpms) sufficient to eject material at a sufficient velocity to create micro- and/or nano-diameter fibers. Apparatuses and methods that may be used to create the polymer fibers and/or polymer structures using centrifugal spinning are described in the following U.S. Published Patent Applications: 2009/0280325; 2009/0269429; 2009/0232920; 2009/0280207 and 2015/0184317, all of which are incorporated herein by reference.

In various embodiments, fibers or particles may be formed from a composition of a polymer and a bone growth promoting agent. In some embodiments, the polymer functions as a substrate for the bone growth promoting agent. The polymer used may be selected based on the type of bone growth promoting agent and the desired delivery of the bone growth promoting agent. In some embodiments, the nanofibminicrofibers may be produced from a bone growth promoting agent mixed with a non-degradable biocompatible polymer. As used herein, the term "biocompatible polymer" refers to a polymer that the body generally accepts without a substantial immune response, which is capable of implantation in biological systems, without causing excessive fibrosis or rejection reactions. Examples of non-degradable biocompatible polymers include, but are not limited to: polysiloxanes (e.g, poly(dimethyl siloxane); copolymers of dimethylsiloxanes and methylvinylsiloxanes; ethylene/vinyl acetate copolymers (EVA); polyethylene; polypropylene; ethylenepropylene copolymers; acrylic acid polymers; ethylene/ethyl acrylate copolymers; polytetrafluoroethylene (PTFE); polyurethanes; polyesters; polybutathene; polyisoprene; poly(methacrylate); polymethyl methacrylate, styrene-butathene-styrene block copolymers; poly(hydroxyethylmethacrylate) (pHEMA); polyvinyl chloride: polyvinyl acetate; polyethers; polyacrylonitriles; polyethylene glycols; polyntethylpentene; polybutathene; polyhydroxy alkanoates; poly(lactic acid), poly(glycolic acid); polyanhydrides; polyorthoesters; hydrophilic hydrogels; cross-linked polyvinyl alcohol; neoprene rubber; butyl rubber; or mixtures thereof.

In some embodiments, fibers or particles may be produced from a bone growth promoting agent mixed with (or contained within) a biodegradable polymer. As used herein, the term "biodegradable" refers to the ability of a substance or material to break down into harmless substances over time by the action of living organisms. Examples of biodegradable polymers include, but are not limited to: polycaprolactone (PCL); poly(glycolic acid (PGA); polylactide (PLA); poly (lactic acid-glycolic acid) (PLGA), poly(dioxanone), poly(3-hydroxybutyrate), poly(3-hydroxyvalerate), poly(valerolactone), poly(tartronic acid), poly((3-malonic acid), and poly[1,6-bis(carboxyphenoxy)hexane]. For PLA, the lactide used to form the polymer has 3 optical isomers (L-lactide, D-lactide, and DL-lactide), the polymers obtained from L-lactide, D-lactide, and DL-lactide are abbreviated to PLLA, PDLA, and PDLLA, respectively. Biodegradable polymers may break down over time when placed in the body and release the bone growth promoting agent. The release rate of the bone growth promoting agent may be controlled by selection of the biodegradable polymer. Typically, a biodegradable polymer will degrade in between 1 to 24 months, depending on the type of polymer used. Accordingly, the release rate of the bone growth promoting agent may be determined by the rate of degradation of the biodegradable polymer.

In some embodiments, particle size of the biodegradable polymer may determine the release rate of the bone growth promoting agent. For instance, larger particle sizes may take longer to degrade and release the bone growth promoting agent. In some embodiments, particles of biodegradable polymer that fill the implant or are coated on struts of the implant have varying rates of degradation in order to release the bone growth promoting agent at various times. The varying rates of degradation may be implemented, for example, by providing biodegradable polymers of varying sizes (e.g., a distribution of sizes) to the implant. In some embodiments, the varying rates of degradation may be implemented by providing a bone growth promoting agent (or a plurality of bone growth promoting agent) in different biodegradable polymers that have different degradation rates.

In some embodiments, various biodegradable polymer particles included in an implant have various bone growth promoting agents associated with them (e.g., contained within the particles). For example, a first biodegradable polymer may contain a first bone growth promoting agent while a second biodegradable polymer may contain a second bone growth promoting agent. In such an example, the first bone growth promoting agent may be released at a rate determined by the first biodegradable polymer while the second bone growth promoting agent is released at a rate determine by the second biodegradable polymer. Various embodiments may be contemplated with varying types and sizes of biodegradable polymers are combined with varying types of bone growth promoting agents.

Table 1 shows some typical biodegradable polymers and the approximate degradation time.

TABLE 1

| Polymer | Approximate Degradation Time |
|---|---|
| Poly(glycolic acid) | 6-12 months |
| Poly(l-lactic acid) | 24 to 36 months |
| Poly(d,l-lactic acid) | 12 to 16 monthsd |
| Poly (d,l-lactic-co-glycolic acid (85/15) | 1 to 6 months |
| Poly(caprolactone) | 24-36 months |

Figure 9:
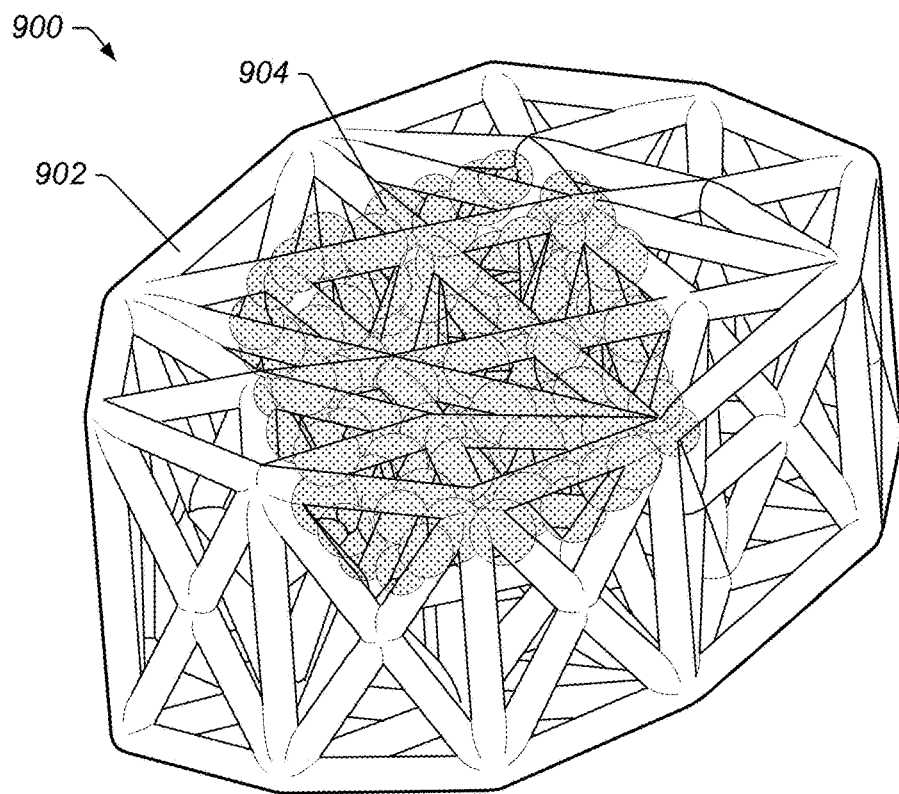
FIG. 9 illustrates an isometric view of an implant filled with particles, according to some embodiments.

As described herein, fibers or particles may be placed in an implant, used to coat the implant, or attached to the struts on an implant. FIG. 9 illustrates an isometric view of an implant filled with particles, according to some embodiments. In the illustrated embodiment, implant 900 includes struts 902 with particles 904 filling portions of the space/volume between the struts. Particles 904 may be positioned in an interior volume of implant 900. In certain embodiments, particles 904 fill or substantially fill the entire interior volume of implant 900. In other embodiments, particles 904 may fill a portion or portions of the interior volume of implant 900.

In various embodiments, particles 904 include microgranules. In some embodiments, particles 904 may be fibers such as polymeric fibers or collagen fibers. In certain embodiments, particles 904 include polymeric substrates (such as biodegradable polymeric substrates) that contain a bone growth promoting agent, as described herein Polymeric substrates may include, for example, biodegradable polymers that release the bone growth agent over time as the polymers degrade. Particles 904 may have a variety of sizes. For example, particles 904 may include microfibers, nanofibers, macrofibers, or a combination thereof. The sizes of particles 904 may, in some embodiments, be determined by the size of the polymeric substrates.

In various embodiments, particles 904 may be placed into implant 900 after formation of the implant. For example, for fibers, a fibrous mat may be collected from the electrospinning or centrifugal spinning process. The mat may be pushed into the web structure of implant 900 such that the fibers are positioned in (e.g., filled or embedded into) an interior volume of the implant In some embodiments, particles 904 may be electrospun into implant 900.

Figure 10:
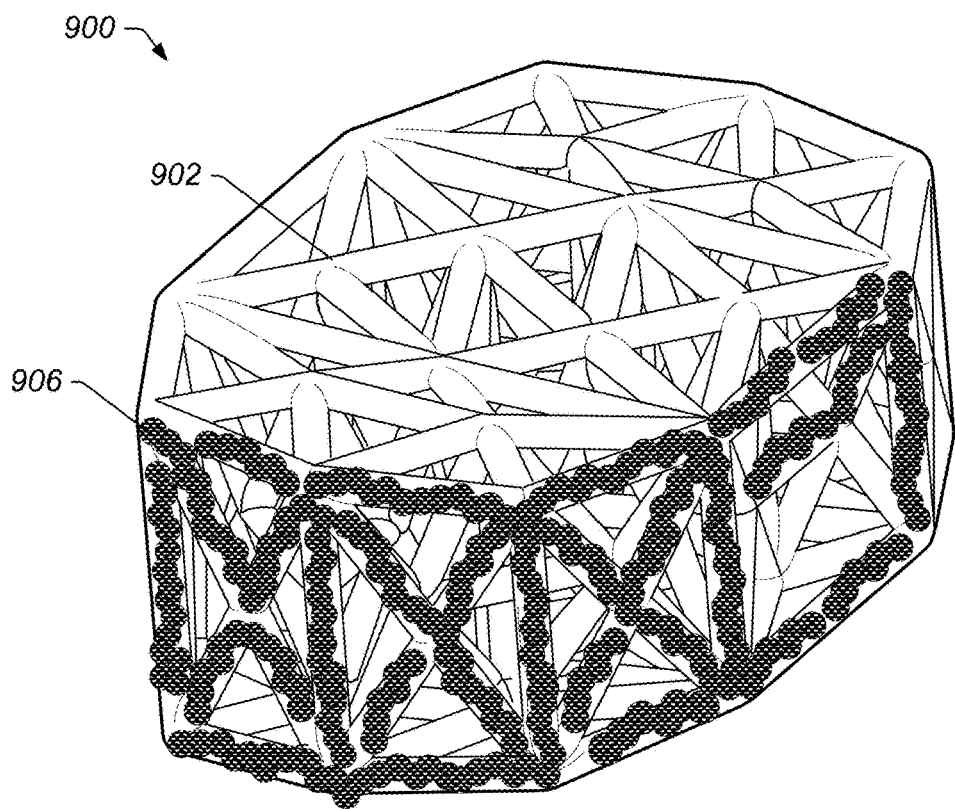
FIG. 10 illustrates an isometric view of an implant with particles (fibers) coating struts of the implant, according to some embodiments.

In some embodiments, particles or fibers are coated on portions of an implant. FIG. 10 illustrates an isometric view of an implant with fibers coating struts of the implant, according to some embodiments. In the illustrated embodiment, implant 900 includes struts 902 coated with fibers 906. Fibers 906 may have a variety of sizes. Examples of fiber sizes include, but are not limited to, microfibers, nanofibers, macrofibers, or combinations thereof. Fibers 906 may include, but not be limited to, collagen fibers, cortical fibers, allograft fibers, synthetic fibers, or combinations thereof.

In various embodiments, fibers 906 are coated on struts 902 on the exterior of implant 900 (e.g., the exterior of the web structure). Fibers 906 may, however, also be coated on struts 902 in the interior of implant 900. Fibers 906 may be coated on any number of struts or all the struts depending on desired properties of implant 900. In various embodiments, as described above, fibers 906 may coat the outside of implant 900 either with or without particles (e.g., particles 904) being positioned in the web structure. For example, in an electrospinning process, the implant may be connected to an electrical source to create an electrical charge on the implant opposite to the electrical charge of the fibers being produced. The charged fibers are therefore attracted to the implant and form a coating on the implant. The elongated fibers produced during the electrospinning process may become wrapped around the struts of a planar truss structure implant during production, coating at least a portion of the exterior surface of the web structure. This process may be used in combination with filling (e.g., embedding) the implant with particles (or other bone growth promoting materials) to form an implant that is filled with particles containing a bone growth promoting agent and coated with fibers.

In some embodiments, fibers 906 are attached to one or more struts 902 of the implant 900. For instance, fibers 906 may be attached to one or more struts 902 by placing the fibers within the web structure of the implant, or coating the implant with the fibers, and heating the fibers to a temperature above the glass transition temperature of the polymer. Heating above the glass transition temperature of the polymer creates melting of the outer surface of the fibers. The at least partially melted fibers will stick to the struts as the melted fibrous material begins to surround the strut. After a sufficient amount of time, the fibers are cooled, returning the fibrous material to a solid state. The cooled fibers are connected to the struts. This method may be used to attach fibers to the interior or exterior of the implant.

In some embodiments, particles or fibers composed of a polymer and a bone growth promoting agent may be used to improve bone growth through and around an implant Particles may be macroparticles, microparticles, and/or nanoparticles. As used herein "macroparticles" refers to particles having an average diameter ranging from about 1 mm to 10 mm. As used herein the term "microparticle" refers to particles having an average diameter ranging from about 1 micrometer to about 1000 micrometers. The term "nanoparticle" refers to particles whose average diameter ranges from about 1 nanometer to about 1000 nanometers. As used herein, the term "panicles" without a qualifier, refers to macroparticles, microparticles, and nanoparticles.

Particles may be formed from non-degradable biocompatible polymer or biodegradable polymers. Bone growth promoting agents, as described earlier, may be incorporated into the polymers during the formation of the particles, or may be coated onto the outer surface of the particles. In one embodiment, a polymer and a bone growth promoting agent may be combined in a solvent forming a homogeneous mixture. The homogenous mixture may be formed into a bulk polymer material. The bulk polymer material may be passed through a milling process to produce particles. The conditions of the milling process may be set to produce macroparticles, microparticles, or nanoparticles, as needed for the particular implant.

During use, the particles may be placed inside the web structure of the implant, as shown in FIG. 9. Alternatively, the particles may be attached to one or more struts of the implant (e.g., such as fibers 906 shown in FIG. 10). In one embodiment, the particles may be attached to one or more struts by placing the particles within the web structure of the implant and heating the particles to a temperature above the glass transition temperature of the polymer. Heating above the glass transition temperature of the polymer creates melting of the outer surface of the polymeric particles. The at least partially melted particles will stick to the struts as the melted polymer begins to surround the strut. After a sufficient amount of lime, the particles are cooled, returning the polymer to a solid state. The cooled polymer is connected to the struts. This method may be used to coat the interior or exterior of the implant with the particles.

In some embodiments, the particles may include a bone growth promoting agent encapsulated in a biocompatible case. The biocompatible case may include, for example, fibrous material or fibers such as collagen, cortical, allograft, or synthetic fibers. The particles may be placed inside the implant. During use, the biological fluids present at the location of the implant will dissolve the biodegradable portions of the particles, allowing the bone growth promoting agents in the particles to interact with the surrounding tissues to promote bone growth throughout the implant.

In various embodiments, the properties of particles or fibers may be modified by incorporating other additives into the fibers. For example, adding carbon materials (e.g., graphene or carbon fibers) to the polymeric fibers or particles can improve the strength of the fibers. Antibiotic compounds may also be incorporated into the fibers or particles to provide a release of antibiotic agents into the tissues surrounding the implant.

The following examples are included to demonstrate preferred embodiments. It should be appreciated by those of skill in the arr that the techniques disclosed in the examples represent techniques discovered by the present inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

Poly(lactide-co-glycolide) (PLGA) and Hyaluronic Acid Particles

A mixture of PLGA and hyaluronic acid were combined in a ratio of 9:1. The resulting mixture was milled to the desired particle size. In one embodiment, the mixture was milled to produce millimeter particles having an average diameter from 1 mm to 10 mm. The millimeter particles were pushed into the web structure of an implant. During use, the PLGA is dissolved by the body fluids in the vicinity of the implant and the hyaluronic acid released within the implant to promote bone growth through and around the implant.

Poly(lactide-co-glycolide) (PLGA) and BMP Particles

PLGA was dissolved in methylene chloride in a 1:15 weight to volume ratio. Solution of PLGA was added dropwise to a 1% solution of polyvinyl alcohol (PVA) in water. The resulting mixture was evaporated while stirring to produce PLGA/PVA microparticles. The particles were treated with a solution of BMP-7 in 50% ethanol/0.01% trifluoracetic acid at a concentration of 0.2 mg BMP-7/mL. In one embodiment, the particles are saturated with the BMP-7 solution and stored as −20 C for 24 hours. After this time, the particles were lyophilized for 24 hours to form particles coated with BMP-7. During use, the BMP-7 coating the surface of the particles is released within the implant to promote bone growth through and around the implant.

Polyvinyl Alcohol Nanofibers Having Hydroxyapatite Particles

An aqueous solution was formed by mixing hydroxyapatite nanoparticles with a PVA polymer and forming a 7 wt % aqueous solution from the mixture. Electrospinning was carried out at room temperature at applied voltages from 3 kV to 20 kV. The resulting nanofibers were placed into an implant. Turing use, the PVA is dissolved by the body fluids in the vicinity of the implant and the hydroxyapatite nanoparticles released within the implant to promote bone growth through and around the implant.

Poly(lactide-co-glycolide) (PLGA) Fibers Coated with Hydroxyapatite

A solution of PLGA was formed by dissolving PLGA in hexafluoro-2-propanol at a weight/volume ration of 15%. Electrospinning was carried out at 10 kV. The PLGA fibers were coated with hydroxyapatite using a dipping method. The PLGA fibers were immersed in a 0.5 M $CaCl_2$ solution for 10 min, rinsed, then immersed in a 0.3 M $NaHPO_4$ solution for 10 min. This cycle was repeated three times. The nanofibers were freeze dried overnight. The resulting hydroxyapatite nanofibers were placed into an implant. During use, the PLGA is dissolved by the body fluids in the vicinity of the implant and the hydroxyapatite nanoparticles released within the implant to promote bone growth through and around the implant, poly (lactic acid-glycolic acid)

Polycaprolactone Nanofibers Having Hydroxyapatite Particles

A solution for electrospinning was formed by mixing hydroxyapatite nanoparticles with polycaprolactone (POL) in 2,2,2-trifluoroethanol at a concentration of 12% w/v. Electrospinning was carried out at an applied voltage of 20 kV. The resulting nanofibers were placed into an implant. During use, the PCL is dissolved by the body fluids in the vicinity of the implant and the hydroxyapatite nanoparticles released within the implant to promote bone growth through and around the implant.

Polycaprolactone/Gelatin Nanofibers Having Hydroxyapatite Particles

A solution for electrospinning was formed by mixing hydroxyapatite nanoparticles with polycaprolactone (PCL) and gelatin in 2,3,2-trifluoroethanol at a concentration of 12% w/v. The weight ratio of PCL to gelatin was 1:1. Electrospinning was carried out at an applied voltage of 20 kV. The resulting nanofibers were placed into an implant. During use, the PCL is dissolved by the body fluids in the vicinity of the implant and the hydroxyapatite nanoparticles released within the implant to promote bone growth through and around the implant.

Polycaprolactone (PCL)/Poly Lactic Acid (PLA) Nanofibers Having Hydroxyapatite Particles A solution for electrospinning was formed by mixing PCL, PLA, and hydroxyapatite (HA) nanoparticles in dichloromethane and dimethylformamide. The weight ratio of PCL/PLA/HA was 2:1:0.1 or 2:1:0.5. The ratio of DCM:DMF was 3:1 (v/v). Electrospinning was carried out and the resulting nanofibers were placed into an implant. During use, the PCL and PLA is dissolved by the body fluids in the vicinity of the implant and the hydroxyapatite nanoparticles released within the implant to promote bone growth through and around the implant.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An implant for interfacing with a bone structure, comprising:
   a web structure comprising a plurality of struts joined at nodes, wherein the web structure is configured to interface with human bone tissue;
   a plurality of biocompatible fibers coated on one or more of the plurality of struts; and
   a plurality of biodegradable particles contained within the biocompatible fibers, the biodegradable particles encapsulating one or more bone growth promoting agents, wherein the biodegradable particles dissolve in the presence of biological fluids in order to release the encapsulated bone growth promoting agents, and wherein the biodegradable particles include particles of varying sizes where different size particles release the encapsulated bone growth promoting at different times in the of the biological fluid.

2. The implant of claim 1, wherein the fibers are contained within an open space of the web structure.

3. The implant of claim 1, wherein the fibers are microfibers, nanofibers, macrofibers, or combinations thereof.

4. The implant of claim 1, wherein the fibers are collagen fibers, cortical fibers, allograft fibers, synthetic fibers, or combinations thereof.

5. The implant of claim 1, wherein the one or more bone growth promoting agents include at least one of calcium phosphate and polysaccharide.

6. The implant of claim 1, further comprising an additional plurality of the biodegradable particles filling a portion of an interior volume of the web structure.

7. The implant of claim 1, wherein the web structure comprises a space truss having two or more planar truss units.

8. The implant of claim 1, wherein the biocompatible fibers are attached to one or more struts on an interior of the web structure.

9. An implant for interfacing with a bone structure, comprising:
   a web structure comprising a plurality of struts joined at nodes, wherein the web structure is configured to interface with human bone tissue;
   a plurality of biocompatible fibers coated on one or more of the plurality of struts; and
   a plurality of biodegradable particles contained within the biocompatible fibers, the biodegradable particles encapsulating one or more bone growth promoting agents, wherein the biodegradable particles dissolve in the presence of biological fluids in order to release the encapsulated bone growth promoting agents, and wherein the biodegradable particles include particles with varying degradation properties in the presence of the biological fluid such that at least some of the biodegradable particles release the encapsulated bone growth promoting agents at different times in the presence of the biological fluid.

10. The implant of claim 9, wherein the fibers are contained within an open space of the web structure.

11. The implant of claim 9, wherein the fibers are microfibers, nanofibers, macrofibers, or combinations thereof.

12. The implant of claim 9, wherein the fibers are collagen fibers, cortical fibers, allograft fibers, synthetic fibers, or combinations thereof.

13. The implant of claim 9, wherein the one or more bone growth promoting agents include at least one of calcium phosphate and polysaccharide.

14. The implant of claim 9, further comprising an additional plurality of the biodegradable particles filling a portion of an interior volume of the web structure.

15. The implant of claim 9, wherein the web structure comprises a space truss having two or more planar truss units.

16. The implant of claim 9, wherein the biocompatible fibers are attached to one or more struts on an interior of the web structure.

* * * * *

UNITED STATES PATENT AND TRADEMARK OFFICE
CERTIFICATE OF CORRECTION

PATENT NO. : 12,279,964 B2
APPLICATION NO. : 17/370781
DATED : April 22, 2025
INVENTOR(S) : Jessee Hunt Page 1 of 1

It is certified that error appears in the above-identified patent and that said Letters Patent is hereby corrected as shown below:

In the Claims

Column 22, Claim 1, Line 62, "promoting at different times" should read -- promoting agents at different times --.

Column 22, Claim 1, Line 63, "in the of the biological fluid." should read -- in the presence of the biological fluid. --.

Signed and Sealed this
Third Day of June, 2025

Coke Morgan Stewart
*Acting Director of the United States Patent and Trademark Office*